US009687286B2

(12) United States Patent
Weiner et al.

(10) Patent No.: US 9,687,286 B2
(45) Date of Patent: Jun. 27, 2017

(54) BONE JOINING APPARATUS AND METHOD

(71) Applicant: Nextremity Solutions, Inc., Red Bank, NJ (US)

(72) Inventors: Lon S. Weiner, Rumson, NJ (US); Stuart D. Katchis, Scarsdale, NY (US); Arthur A. Alfaro, Colts Neck, NJ (US); Willem H. P. Van Iperen, Westfield, NJ (US); Mari S. Truman, Warsaw, IN (US)

(73) Assignee: NEXTREMITY SOLUTIONS, INC., Warsaw, IN (US)

( * ) Notice: Subject to any disclaimer, the term of this patent is extended or adjusted under 35 U.S.C. 154(b) by 313 days.

(21) Appl. No.: 14/270,542

(22) Filed: May 6, 2014

(65) Prior Publication Data

US 2014/0243910 A1 Aug. 28, 2014

Related U.S. Application Data

(63) Continuation of application No. 12/709,426, filed on Feb. 19, 2010, now Pat. No. 8,715,325.

(Continued)

(51) Int. Cl.
*A61B 17/86* (2006.01)
*A61B 17/16* (2006.01)
(Continued)

(52) U.S. Cl.
CPC ...... *A61B 17/8685* (2013.01); *A61B 17/1682* (2013.01); *A61B 17/68* (2013.01); *A61F 2/4225* (2013.01); *A61F 2/4606* (2013.01); *A61B 17/7291* (2013.01); *A61B 17/86* (2013.01); *A61F 2002/3085* (2013.01); *A61F 2002/30205* (2013.01); *A61F 2002/30331* (2013.01); *A61F 2002/30481* (2013.01); *A61F 2002/30487* (2013.01); *A61F 2002/30497* (2013.01); *A61F 2002/30538* (2013.01);
(Continued)

(58) Field of Classification Search
CPC .......................... A61B 17/86; A61B 17/8685
USPC .................................................. 606/300–331
See application file for complete search history.

(56) References Cited

U.S. PATENT DOCUMENTS 3,991,425 A 11/1976 Martin et al.
4,246,662 A 1/1981 Pastrick
(Continued)

FOREIGN PATENT DOCUMENTS

DE 19949890 A1 6/2001
EP 0524874 A1 1/1993
(Continued)

OTHER PUBLICATIONS

Restriction Requirement in U.S. Appl. No. 12/709,426, dated May 15, 2012, 8 pages.
(Continued)

*Primary Examiner* — Christopher Beccia
(74) *Attorney, Agent, or Firm* — Heslin Rothenberg Farley & Mesiti P.C.; John W. Boger

(57) ABSTRACT

Provided is a bone joining device suitable for joining a first bone piece to a second bone piece. Also provided is a method of joining a first bone piece with a second bone piece in a living mammal. The method comprises inserting the above bone joining device between the first bone piece and the second bone piece.

20 Claims, 34 Drawing Sheets

Related U.S. Application Data

(60) Provisional application No. 61/153,907, filed on Feb. 19, 2009.

(51) Int. Cl.
*A61B 17/68* (2006.01)
*A61F 2/42* (2006.01)
*A61F 2/46* (2006.01)
A61F 2/30 (2006.01)
A61B 17/72 (2006.01)

(52) U.S. Cl.
CPC ............... *A61F 2002/30551* (2013.01); *A61F 2002/30622* (2013.01); *A61F 2002/30624* (2013.01); *A61F 2002/30874* (2013.01); *A61F 2002/423* (2013.01); *A61F 2002/4235* (2013.01); *A61F 2220/0025* (2013.01); *A61F 2220/0033* (2013.01); *A61F 2230/0067* (2013.01); *A61F 2250/0006* (2013.01)

(56) References Cited

U.S. PATENT DOCUMENTS

| | | |
|---|---|---|
| 4,304,011 A | 12/1981 | Whelan, III |
| D277,784 S | 2/1985 | Sgarlato et al. |
| 4,908,031 A | 3/1990 | Frisch |
| 5,037,440 A | 8/1991 | Koenig |
| 5,062,851 A | 11/1991 | Branemark |
| 5,129,903 A | 7/1992 | Luhr et al. |
| 5,167,661 A | 12/1992 | Wagenknecht |
| 5,207,712 A | 5/1993 | Cohen |
| 5,290,314 A | 3/1994 | Koch et al. |
| 5,417,692 A | 5/1995 | Goble et al. |
| 5,443,467 A | 8/1995 | Biedermann et al. |
| 5,683,466 A | 11/1997 | Vitale |
| 5,725,581 A | 3/1998 | Branemark |
| 5,810,591 A | 9/1998 | Huber |
| 5,810,822 A | 9/1998 | Mortier |
| 5,827,285 A | 10/1998 | Bramlet |
| 5,919,193 A | 7/1999 | Slavitt |
| 6,099,571 A | 8/2000 | Knapp |
| 6,284,001 B1 | 9/2001 | Knapp |
| 6,383,223 B1 | 5/2002 | Baehler et al. |
| 6,413,260 B1* | 7/2002 | Berrevoets ............. A61B 17/68 606/304 |
| 6,454,808 B1 | 9/2002 | Masada |
| 6,458,134 B1* | 10/2002 | Songer ................... A61B 17/68 606/304 |
| 6,517,543 B1 | 2/2003 | Berrevoets et al. |
| 6,602,293 B1 | 8/2003 | Biermann et al. |
| 6,852,113 B2 | 2/2005 | Nathanson et al. |
| 6,964,994 B1 | 11/2005 | Antonietti et al. |
| 7,041,106 B1 | 5/2006 | Carver et al. |
| 7,214,226 B2 | 5/2007 | Alleyne |
| 7,291,175 B1 | 11/2007 | Gordon |
| 7,297,165 B1 | 11/2007 | Kriek |
| 7,611,526 B2 | 11/2009 | Carl et al. |
| 7,635,364 B2 | 12/2009 | Barrall et al. |
| 7,837,738 B2 | 11/2010 | Reigstad et al. |
| 8,100,983 B2 | 1/2012 | Schulte |
| 8,303,589 B2 | 11/2012 | Tyber |
| 8,313,487 B2 | 11/2012 | Tyber |
| 8,328,806 B2 | 12/2012 | Tyber |
| 8,715,325 B2 | 5/2014 | Weiner |
| 2004/0127900 A1 | 7/2004 | Konieczynski et al. |
| 2004/0220678 A1* | 11/2004 | Chow ................... A61F 2/4241 623/21.11 |
| 2005/0043732 A1 | 2/2005 | Dalton |
| 2005/0113830 A1 | 5/2005 | Rezach et al. |
| 2005/0192587 A1 | 9/2005 | Lim |
| 2006/0052878 A1 | 3/2006 | Schmieding |
| 2006/0074492 A1 | 4/2006 | Frey |
| 2006/0195087 A1 | 8/2006 | Sacher et al. |
| 2008/0045963 A1 | 2/2008 | Abdou |
| 2008/0065224 A1 | 3/2008 | Reigstad et al. |
| 2008/0097611 A1 | 4/2008 | Mastrorio et al. |
| 2008/0177321 A1* | 7/2008 | Drewry ............. A61B 17/7032 606/266 |
| 2009/0157121 A1 | 6/2009 | Harris et al. |
| 2010/0036439 A1 | 2/2010 | Lavi |
| 2010/0121325 A1 | 5/2010 | Tyber |
| 2010/0256638 A1 | 10/2010 | Tyber |
| 2011/0004255 A1 | 1/2011 | Weiner et al. |
| 2011/0054545 A1 | 3/2011 | Champagne |
| 2011/0082508 A1 | 4/2011 | Reed |
| 2011/0118739 A1 | 5/2011 | Tyber |
| 2011/0125153 A1 | 5/2011 | Tyber |
| 2013/0030475 A1 | 1/2013 | Weiner et al. |
| 2013/0274814 A1 | 10/2013 | Weiner et al. |

FOREIGN PATENT DOCUMENTS

| | | |
|---|---|---|
| EP | 0831757 B1 | 11/2001 |
| EP | 1632200 A1 | 8/2006 |
| FR | 2651119 A1 | 3/1991 |
| GB | 1582974 A | 1/1981 |
| GB | 2126097 A | 3/1984 |
| JP | 2005073740 A | 3/2005 |
| WO | 9309728 A1 | 5/1993 |
| WO | 9605784 A1 | 2/1996 |
| WO | 9716137 A1 | 5/1997 |
| WO | 0200123 A1 | 1/2002 |
| WO | 2007109752 A2 | 9/2007 |
| WO | 2009018527 A1 | 2/2009 |
| WO | 2010096724 A1 | 8/2010 |
| WO | 2011025900 A1 | 3/2011 |

OTHER PUBLICATIONS

Office Action in U.S. Appl. No. 12/709,426, dated Jul. 3, 2012, 11 pages.
Final Office Action in U.S. Appl. No. 12/709,426, dated Oct. 31, 2012, 11 pages.
Caterini et al., "Arthrodesis of the toe joints with an intramedullary cannulated screw for correction of hammertoe deformity", Foot & Ankle International, 2004, pp. 256-261, vol. 25, No. 4.
Edwards and Beischer, "Interphalangeal joint arthodesis of the lesser toes", Foot & Ankle Clinics North America, 2002, pp. 43-48, vol. 7.
Hetherington, "Metatarsalgia and lesser metatarsal surgery", Hallux Valgus and Forefront Surgery textbook, 2000, pp. 429-451.
International Search Report dated Jul. 9, 2010 in related PCT Application No. PCT/US1024833, 6 pages.
Iselin et al., "Desarthrodeses-arthroplasties interphalangiennes proximales"—"Conversion to Arthroplasty from Proximal Interphalangeal Joint Arthrodesis", Annales de Chirurgie de la Main, 1988, pp. 115-119, vol. 7, No. 2.
Konkel et al., "Hammer toe correction using an absorbable intramedullary pin", Foot & Ankle International, 2007, pp. 916-920, vol. 28, No. 8.
Murray, "Surface Replacement Arthroplasty of the Proximal Interphalageal Joint", The Journal of Hand Surgery, 2007, pp. 899-904, vol. 32A, No. 6.
Ship Implant Brochure, Sgarlato Hammertoe Implant Procedure, Sgarlato Labs, Campbell, CA, 2006, 2 pages.
Sokolow, "Une prothese de l'articulation interphalangienne proximale osteo-integree: IPP 2. Premiers resultants"—"Short term results of the IPP 2 proximal interphalangeal joint prosthesis", Chirurgie de la Main, 2006, pp. 280-285, vol. 25, abstract only in English.
Supplementary European Search Report dated Jun. 2, 2014 in related EP Application No. 10744409.3, 6 pages.
European Search Report dated Jan. 2, 2014 in related EP Application No. 13186873.9, 6 pages.
European Search Report dated Feb. 20, 2014 in related EP Application No. 13187042.0, 6 pages.

* cited by examiner

A

B

BONE JOINING APPARATUS AND METHOD

CROSS-REFERENCE TO RELATED APPLICATIONS

This application is a continuation application of U.S. application Ser. No. 12/709,426, filed on Feb. 19, 2010 and issued on May 6, 2014 as U.S. Pat. No. 8,715,325, which claims the benefit of U.S. Provisional Application No. 61/153,907, filed Feb. 19, 2009, which are each incorporated herein by reference in their entirety.

BACKGROUND (1) Field

This application relates to devices and methods for joining bones.

(2) Description of the Related Art

Hammertoe deformity, the most common deformity of the lesser toes, is a flexion deformity of the proximal interphalangeal (PIP) joint of the toe, with hyperextension of the metatarsophalangeal (MTP) and distal interphalangeal (DIP) joints. Progressive PIP joint flexion deformity typically leads to compensatory hyperextension of the MTP and DIP joints. This makes the PIP joint prominent dorsally. Pain occurs due to rubbing of the prominence against the patient's shoe. The deformity is flexible at first but usually becomes fixed over time. When the deformity is flexible, various procedures can be utilized that involve manipulation of the involved tendons. However, when the deformity is fixed, PIP fusion or joint replacement is often required. Implants available for this purpose include the Weil-Carver™ Hammertoe Implant (Biomet®, Inc., Warsaw, Ind.), Flexible Digital Implant (Tornier, Inc. Edina, Minn.), SHIP Implant (Sgarlato Labs, Campbell Calif.), Digital Compression Screw (BioPro®, Port Huron Mich.), Smart Toe™ Intramedullary Memory Implant (Memometal Inc., Memphis Tenn.) and StayFuse™ Intramedullary Fusion Device (Tornier, Inc. Edina, Minn.). The latter three implants are used when fusion is desired, since the other implants allow some flexibility of the joint. With all current implants, placement is critical because, when mounted, there is no adjustability in the angle of flexion between the two cut bones to be joined.

There is thus a need for alternative designs for implants for joining two bone pieces, including implants that fix the two bone pieces, particularly designs that allow adjustment of the angle of flexion between the two bones. The present invention addresses that need.

BRIEF SUMMARY OF THE INVENTION

A bone joining device is provided that allows adjustment of the angle between the two bones to be joined.

In some embodiments, a bone joining device suitable for joining a first bone piece to a second bone piece is provided. The device comprises a first component and a second component, wherein the first component comprises a first elongated stem portion comprising a first end and a first top opposite the first end, the first stem portion suitable for insertion from the first end longitudinally into a surface of the first bone piece, and the second component comprises a second elongated stem portion comprising a second end and a second top, the second stem portion suitable for insertion from the second end longitudinally into a surface of the second bone piece. The device also comprises a connector extending from the second top, wherein the connector is capable of linking with the first component and locking therewith.

Also provided is a pin locking tool suitable for locking a position of the connector in relation to the second top in the above-described device. The pin locking tool comprises a handle comprising a thumb hole and finger hole pivotally joined by a scissor hinge to bring together a first distal end and a second distal end when the thumb hole and finger hole are pulled together; the first distal end terminated by a contoured formation which is configured to engage the second top; the second distal end terminated by a pin formation configured to engage the wide end of the locking pin.

Additionally, a tool for reaming a hole from a cut bone surface into an intramedullary canal of the bone is provided. The tool comprises an elongate first shank having a first proximal end and a first distal end, the distal end terminating in a shaping drill end terminating in a point, the shaping drill further comprising a plurality of first ridges having sharp edges immediately proximal to the point; a short shaft immediately proximal to the first ridges; a shoulder wider than the short shaft immediately proximal to the short shaft; a skirt having a distal surface, wider than the shoulder immediately proximal to the shoulder having a concave or a convex distal surface; and a cutout extending from the plurality of ridges through the first short shaft, the first shoulder, and the first skirt, the cutout having sharp lateral edges designed to cut through the bone as the tool is rotated and driven therein.

Additionally, a driver suitable for screwing the above-described device into an intramedullary canal of a bone is provided. The device comprises an elongate shank having a proximal end and a distal end. The distal end comprises two half sections operably linked to a slidable bobbin on the shank, such that sliding the bobbin toward the distal end forces the two half sections together to hold the first top or the second top securely.

Also provided is a method of joining a first bone piece with a second bone piece in a living vertebrate. The method comprises inserting the above-described bone joining device between the first bone piece and the second bone piece such that the two bone pieces are securely joined.

DETAILED DESCRIPTION OF THE INVENTION

Figure 1:
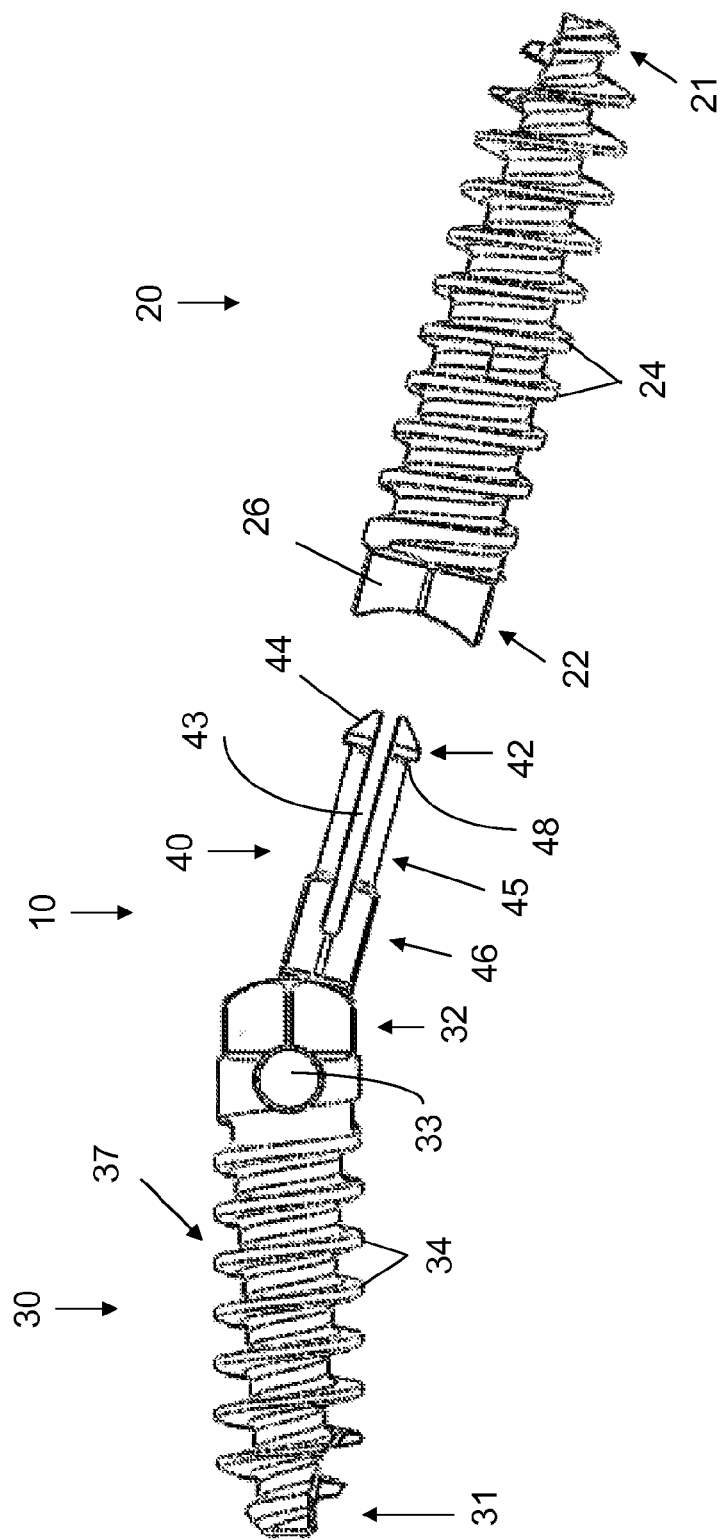
FIG. 1 is a perspective view of one embodiment of the invention bone joining device showing the female component and the male component aligned for joining.
Figure 2:
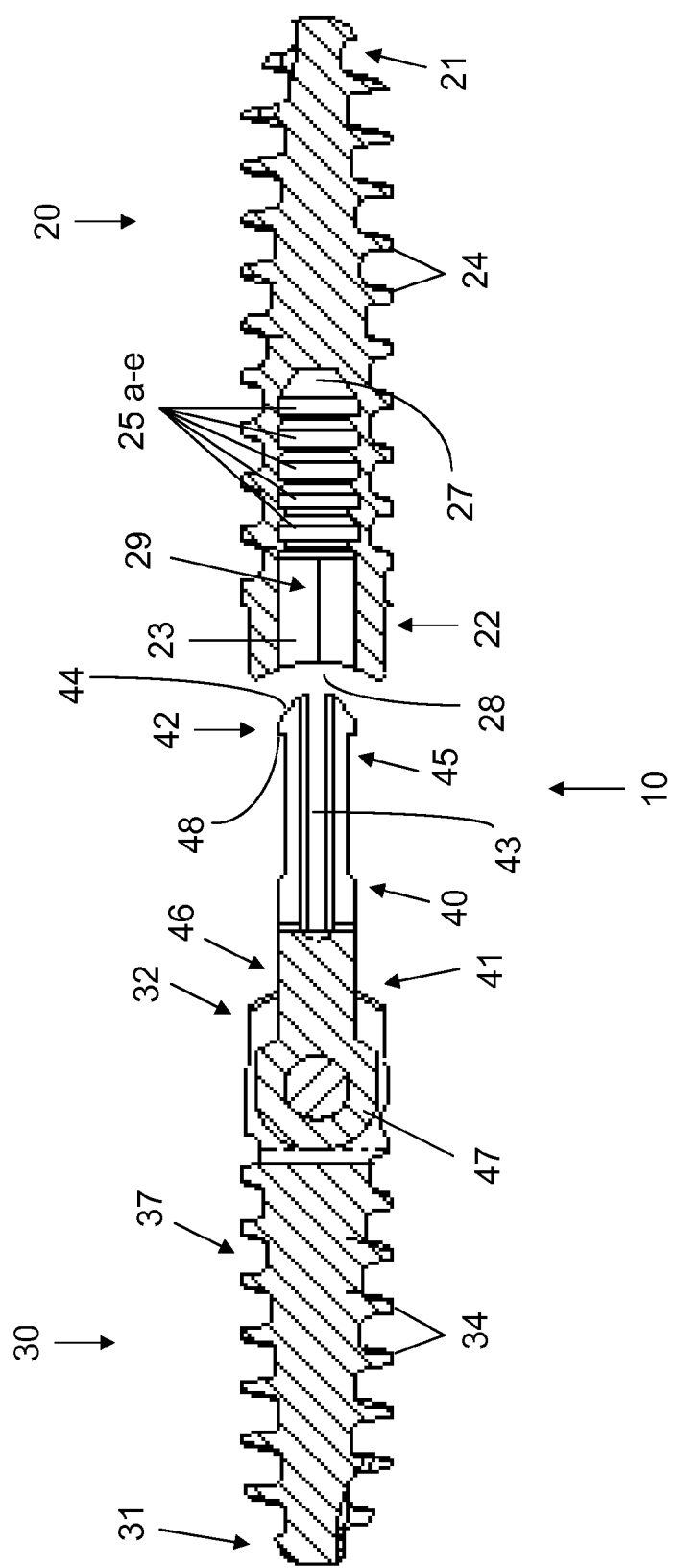
FIG. 2 is a sectional view of one embodiment of the invention bone joining device showing the female component and the male component aligned for joining.

The inventors have developed a bone joining device that allows adjustment of the angle between the two bones to be joined.

In some embodiments, the application is directed to a bone joining device suitable for joining a first bone piece to a second bone piece. The device comprises a first component and a second component, wherein the first component comprises a first elongated stem portion comprising a first end and a first top opposite the first end, the first elongated stem portion suitable for insertion from the first end longitudinally into a surface of the first bone piece, and the second component comprises a second elongated stem portion comprising a second end and a second top, the second elongated stem portion suitable for insertion from the second end longitudinally into a surface of the second bone piece. The device further comprises a connector extending from the second top. The connector is capable of joining with the first component and locking therewith.

The connector may join with the first component by any means known in the art. Non-limiting examples of such joining means include knobs, clamps, teeth, glues, Velcro® and staples. In some embodiments, the first component is a female component and the second component is a male component, wherein the first elongated stem portion of the female component further comprises an opening that extends axially from the first top toward the first end; and the connector comprises an elongated shaft, a proximal end, a top of shaft near the proximal end, and a distal end, wherein the connector is capable of insertion into the opening in the first elongated stem portion and locking therein. The figures provide several examples of these devices, as detailed below.

The device is generally useful for joining any two bone pieces, for example two vertebrae or two halves of a broken bone. In some embodiments, the device is particularly useful for joining or fusing cut surfaces of bones, in particular the cut ends of long bones, especially fingers or toes, e.g., for joining or fusing a joint on a lesser toe, for example to treat hammertoe, claw toe, mallet toe or curly toe. In those embodiments, the first stem portion is suitable for insertion from the first end longitudinally into a cut surface of a resected phalanx, metatarsal or metacarpal, or a cut diaphysis, and the second stem portion is suitable for insertion from the second end longitudinally into a cut surface of a resected phalanx, metatarsal or metacarpal, or a cut diaphysis. The device can also be used to fuse a metatarsal that has been shortened by resection.

Various, nonlimiting embodiments of the device are shown in FIGS. 1-33, where the bone joining device 10 is provided as a female component 20 and a male component 30. The female component 20 of this embodiment is an elongated stem, and comprises a first end 21, a first top 22 and a cylindrical cavity 29, best shown in FIGS. 2, 13, 14 and 22, comprising a cylindrical wall 23, a closed distal end 27 and an open proximal end 28. The illustrated female component 20 also comprises a continuous spiraling thread 24 on the exterior of the component, suitable for screwing the component into a bone. The female component 20 is also referred to herein as the "first elongated stem portion." The cavity and wall can have any shape cross section as defined by the cavity wall, including, for example, circular, oval, rectangular hexagonal and octagonal.

The male component 30, best shown in FIGS. 1, 2, 4, 7, 10, 11, 12, 15, 18 and 23, comprises a second elongated stem portion 37 comprising a second end 31 and a second top 32, with a connector 40 extending from the second top 32. The male component 30 is also referred to herein as the "second elongated stem portion." The illustrated second elongated stem portion 37 comprises a continuous spiraling thread 34 on the exterior, where the thread is suitable for screwing the component into a bone 50.

The female component 20 and the male component 30 can independently be cylindrical or conical, or any combination thereof, e.g., cylindrical at the proximal end, transitioning into a conical shape.

While the illustrated embodiments show a spiraling thread as a means to anchor the male component and the female component into the bone, any alternate anchoring means can be used, for example barbs, a shape memory expanding means (e.g., as featured in the Smart Toe™ Implant (Memometal Inc., Memphis Tenn.), or any other anchoring means known in the art.

Where present, the spiraling threads on the device can be of any type known in the art for screwing into a bone. In some embodiments, the spiraling thread is a continuous spiraling thread. In other embodiments, the spiraling thread allows self-tapping and/or self-threading of the first elongated stem portion into the first bone piece and the second elongated stem portion into the second bone piece. See, e.g., 240 of FIGS. 15-17.

In some embodiments, the continuous spiraling thread 24 and 34 on the female and male components both spiral in the same direction, e.g., clockwise, so that, when the device is screwed into opposing bone surfaces and then joined, the opposing pitch of the threads in the bone prevents the device from unscrewing.

These embodiments are not limited to any particular pitch of one rotation of the continuous spiraling thread. For example, the pitch may be 5 mm or greater, 4 mm, 3 mm, 2 mm, 1 mm, less than 1 mm, or any distance in between these distances.

Figure 11:
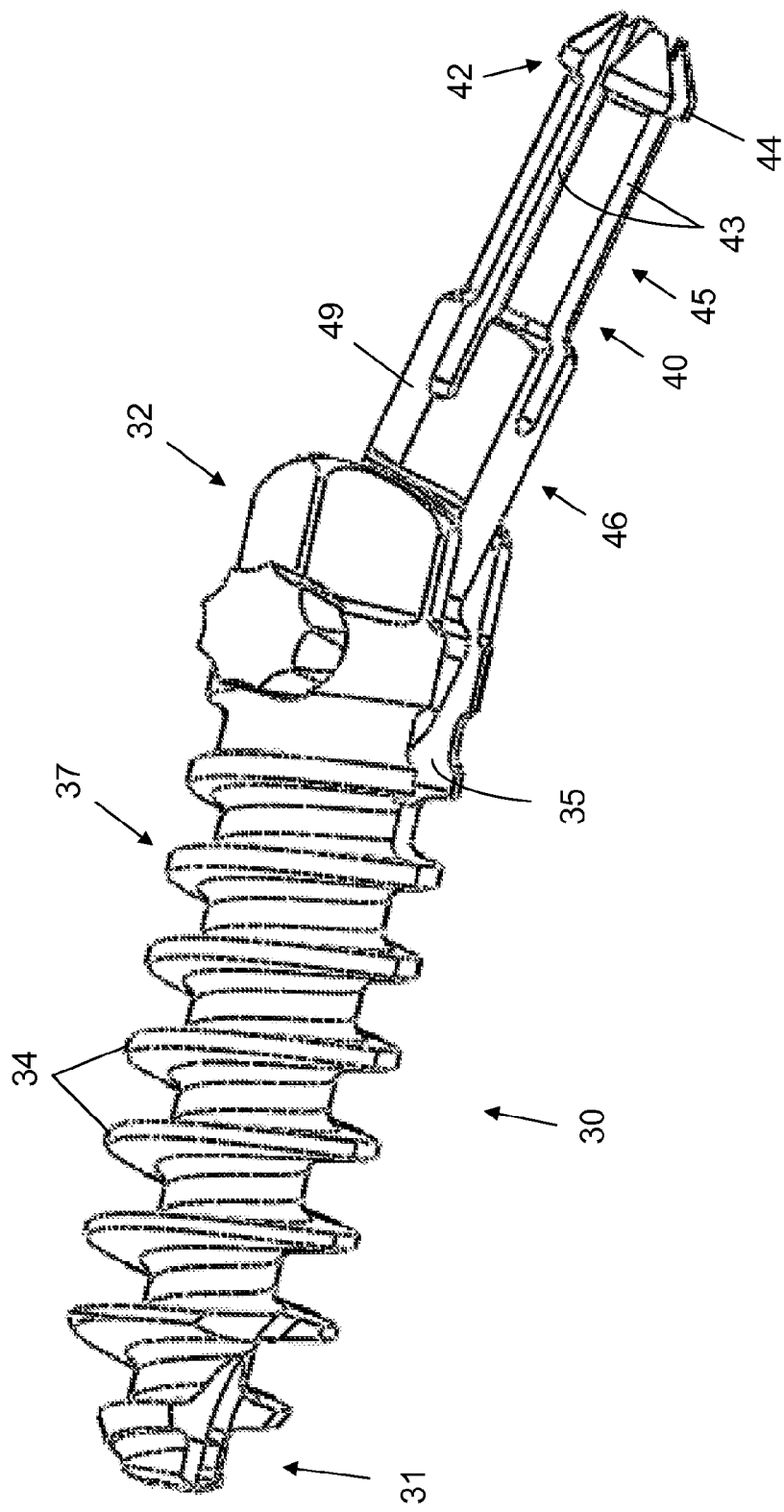
FIG. 11 is a perspective view of one embodiment of the male component of the invention bone joining device.
Figure 12:
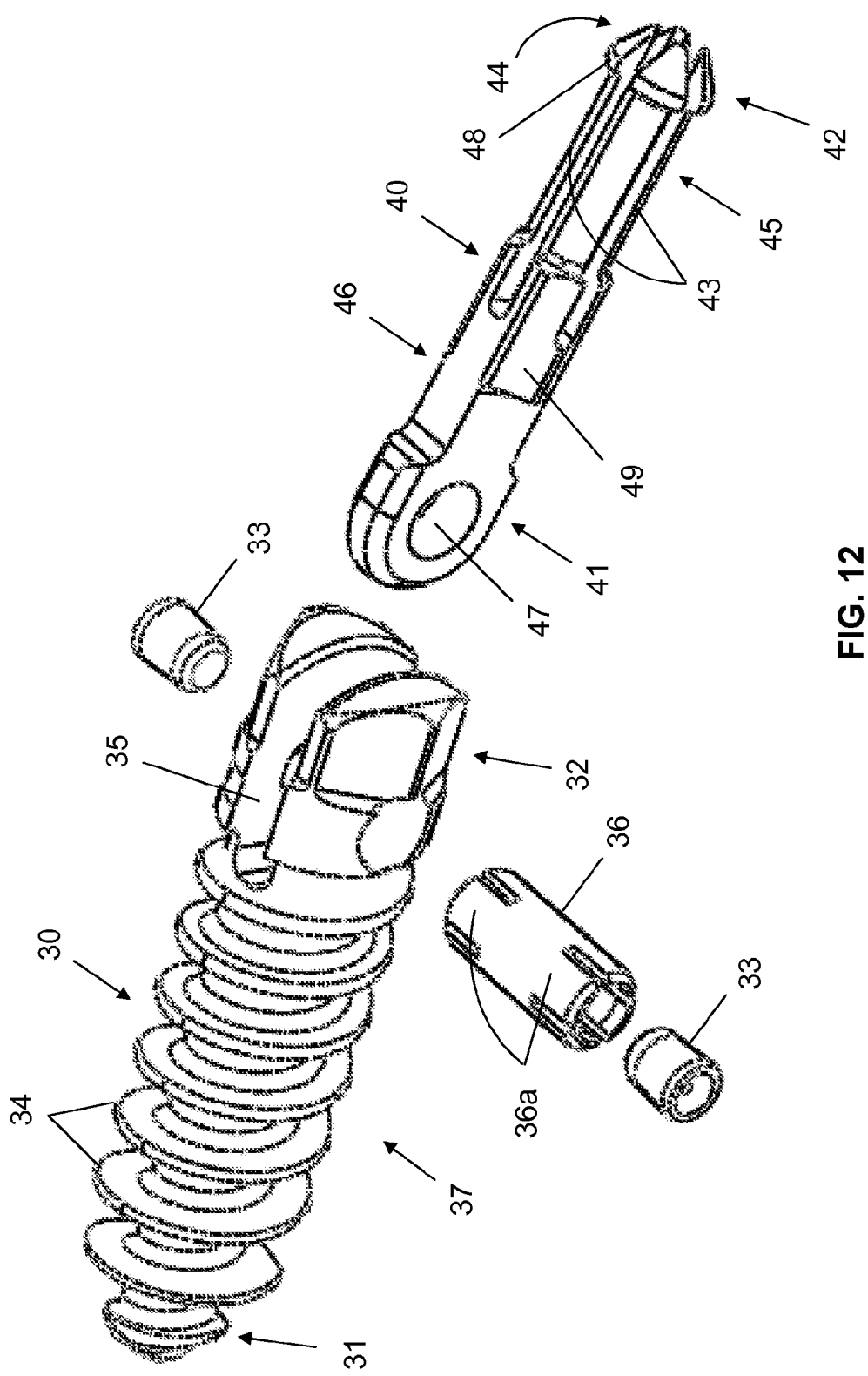
FIG. 12 is an exploded perspective view of one embodiment of the male component of the invention bone joining device.

In some embodiments, the connector 40 is as shown in FIGS. 1, 11 and 12. In those embodiments, the connector 40 extends from the second top 32 and comprises a proximal end 41, a top of shaft 46 near the proximal end 41, and a distal end 42. The proximal end 41 comprises a connector hole 47, best shown in FIG. 12, that is joined to the second top 32 in a recess 35 with crimping pins 33 and a crimping shaft 36. When so joined, the connector 40 can be adjustably positioned in an angular direction in relation to the second top 32 until the crimping pins 33 are crimped toward each other along the crimping shaft 36, forcing outer flanges 36a outward, which engage the connector hole 47, causing friction between the outer flanges 36a and the connector hole 47 and preventing further adjustable positioning of the connector 40 in relation to the second top 32.

The connector hole 47 in combination with the crimping shaft 36 serves as a locking mechanism that prevents adjustable positioning of the connector 40 in relation to the second top. In use, the distal end 42 of the connector 40 is inserted into the open proximal end 28 of the female component 20, penetrating the cylindrical cavity 29 to a certain point, e.g., as in FIGS. 3-7 and 16. This partial insertion feature allows the connector 40 to then be adjusted to the desired angle in relation to the second top 32 before the device is inserted to its final position. The crimping pins 33 are then crimped, using any tool that can push the two crimping pins 33 simultaneously into the crimping shaft 36, preventing further angular movement in relation to the second top. The connector 40 is then further inserted into the shaft to the desired final position.

Figure 19:
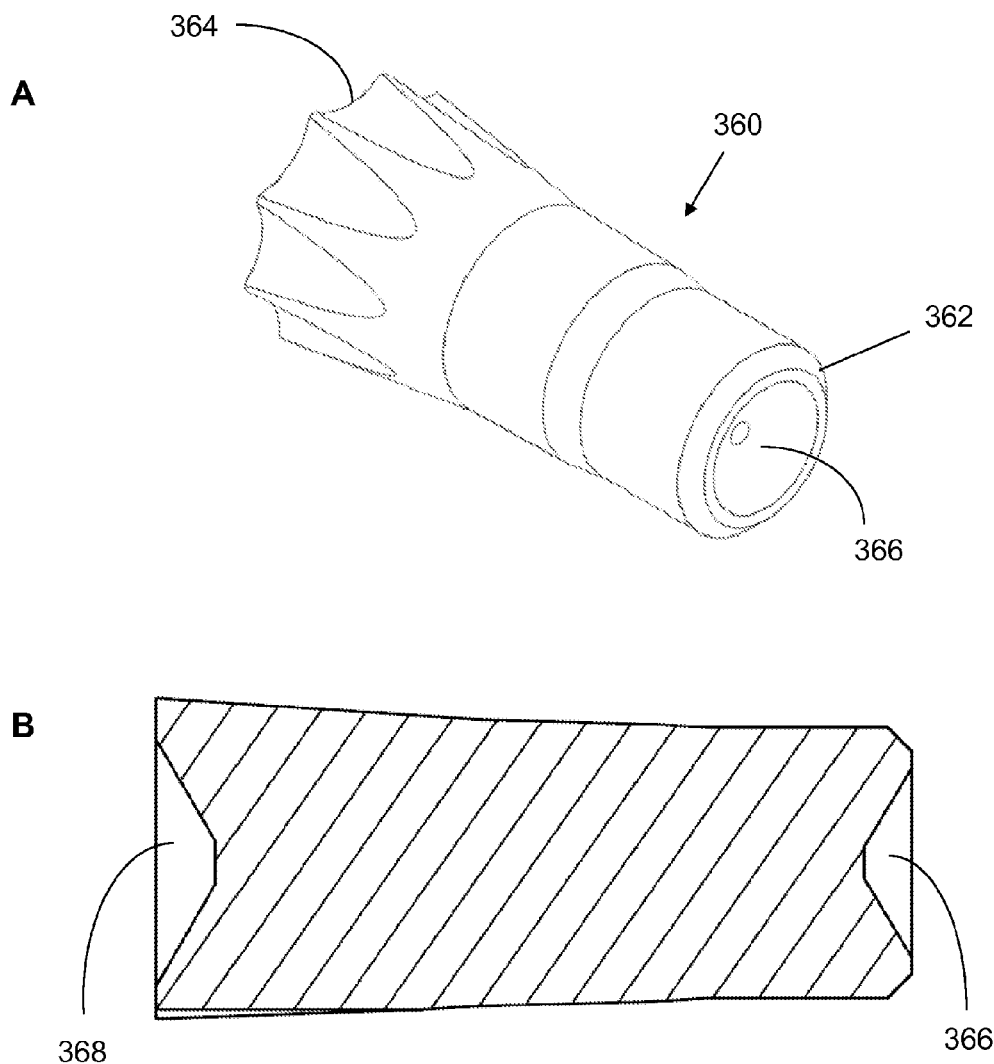
FIG. 19 is a perspective (Panel A) and a cross-sectional (Panel B) view of one embodiment of a crimping shaft of the invention bone joining device.

An alternative embodiment to a crimping shaft to prevent positioning of a connector 40 in relation to a second top 32 is illustrated in FIG. 19. As illustrated therein, the crimping shaft is substituted with a locking pin 360 that has a tapered cylindrical shape having a narrow end 362 and a wide end 364. Although the ends can be of any appropriate configuration, in the illustrated embodiment, both the narrow end 362 and the wide end 364 have inwardly directed indentations 366, 368, which is designed to accommodate a tool used to push the locking pin 360 into the connector hole 47. In use, the locking pin 360 is inserted partly into the connector hole 47 from the narrow end 362, where it acts as an hinge that connects the proximal end 41 of the connector 40 with the second top 32 of the second elongated stem portion 37, allowing angular positioning of the connector 40 in relation to the second top 32. When the connector 40 is in the desired angular position in relation to the second top 32, the wide end 364 of the locking pin 360 is pushed further into the connector hole 47, causing friction between the wide end 364 of the locking pin 360, the connector hole 47, and the second top 32 of the second elongated stem portion 37, frictionally preventing further movement of the connector 40 in relation to the second top 32.

Figure 20:
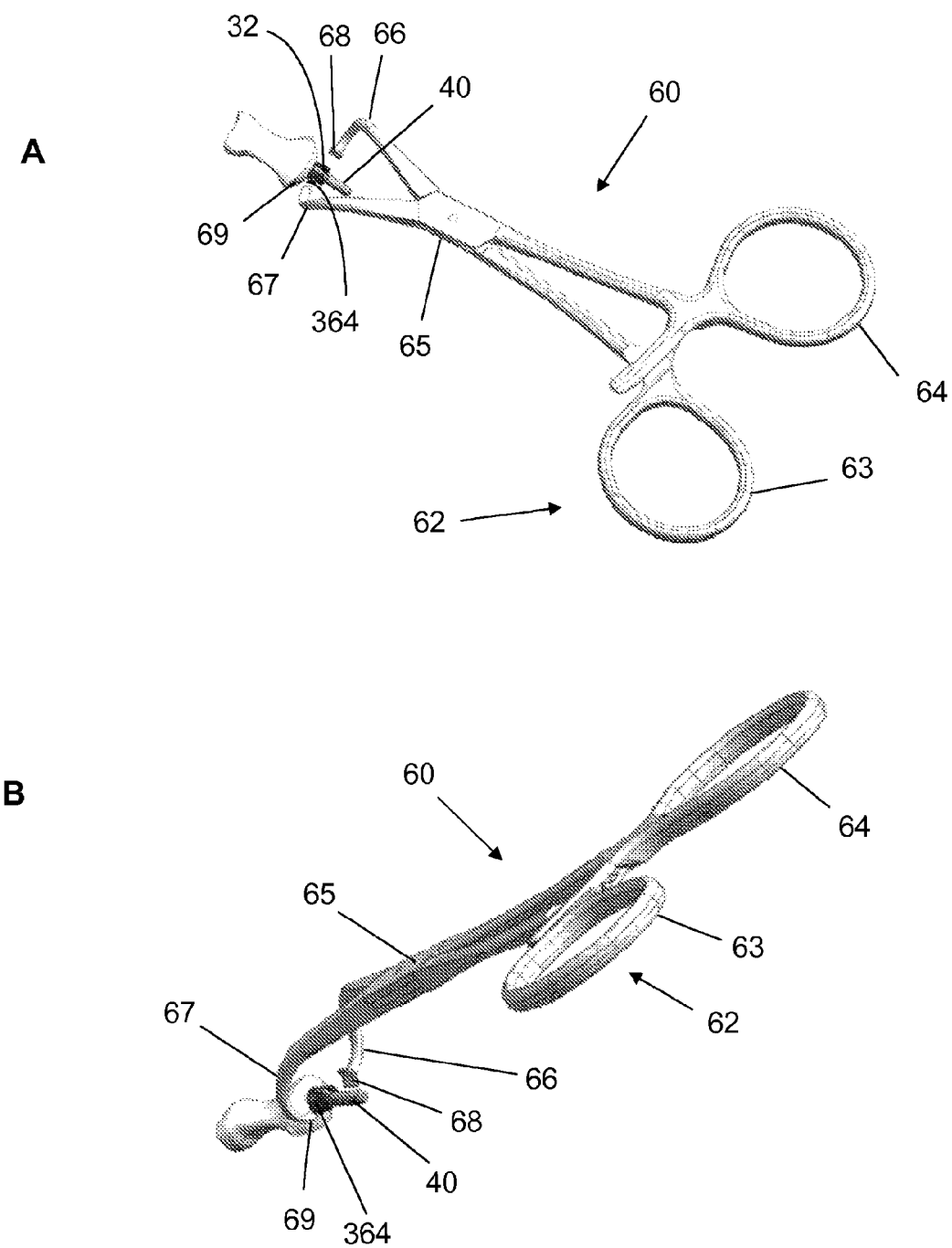
FIG. 20 is two perspective views of one embodiment of a pin locking tool.

In these embodiments, the locking pin 360 can be pushed into the connector hole 47 using any suitable tool, for example a modified tissue clamp, a modified k-wire pliers, or the pin locking tool 60 illustrated in FIG. 20. As illustrated, the pin locking tool 60 comprises a handle 62 comprising a thumb hole and finger hole 63, 64 pivotally joined by a scissor hinge 65 to bring together distal ends 66, 67 when the thumb hole and finger hole 63, 64 are pulled together. Distal end 66 is terminated by a contoured formation 68, which is configured to engage the second top 32. Distal end 68 is terminated by a pin formation 69, which is configured to engage the wide end 364 of the locking pin 360. In that position, when the surgeon pulls the thumb hole and finger hole 63, 64 together, the pin formation 69 pushes the wide end 364 of the locking pin 360 into the connector hole 47, locking the connector 40 in the desired angular position in relation to the second top 32. Although FIG. 20 shows the engagement of the locking pin 360 before the connector 40 is joined to the female component 20, the locking pin 360 can also be so engaged after the connector 40 is so joined, e.g., after the connector 40 is partially inserted into the female component 20, as illustrated in FIGS. 3-7. Additionally, the pin locking tool 60 can be used with the crimping pins 33 and a crimping shaft 36 described above and illustrated in FIG. 12, or with any other suitable component.

In some embodiments, the angle of the connector 40 is not locked in relation to the second top 32, e.g., when fixation is not desired, allowing flexion between the bone pieces such that the connector 40-second top 32 forms a joint, for example a PIP, a DIP or an MTP joint. In these embodiments, the locking pin 360 or crimping pin 33/crimping shaft 36 is not pushed into the connector hole 47, or is only pushed in part way, to allow the desired degree of flexion. Alternatively, a simple pin or any other component can be inserted into the connector hole rather than the locking pin 360 or crimping pin 33/crimping shaft 36, to provide a hinge for the joint.

The connector hole 47 and/or crimping shaft 36 can be designed so that the connector 40 is limited in angular movement in relation to the second top 32. In some embodiments, the connector 40 is capable of being adjustably positioned at an angle of at least 10° in each of a forward direction and a reverse direction in relation to the second top 32. In other embodiments, the connector 40 is capable of being adjustably positioned at an angle of at least 90° in each of a forward direction and a reverse direction in relation to the second top 32. See FIG. 6. In additional embodiments, the connector 40 is capable of being adjustably positioned at an angle of at least 120° in each of a forward direction and a reverse direction in relation to the second top 32. In still other embodiments, the connector 40 is capable of being adjustably positioned at an angle of at least 150° in each of a forward direction and a reverse direction in relation to the second top 32.

In alternative embodiments, the connector 40 is coupled to the second top 32 using a snap-lock, where the connector 40 can lock in the first elongated stem portion 20 without further insertion of the connector 40 into the first elongated stem portion 32.

Figure 13:
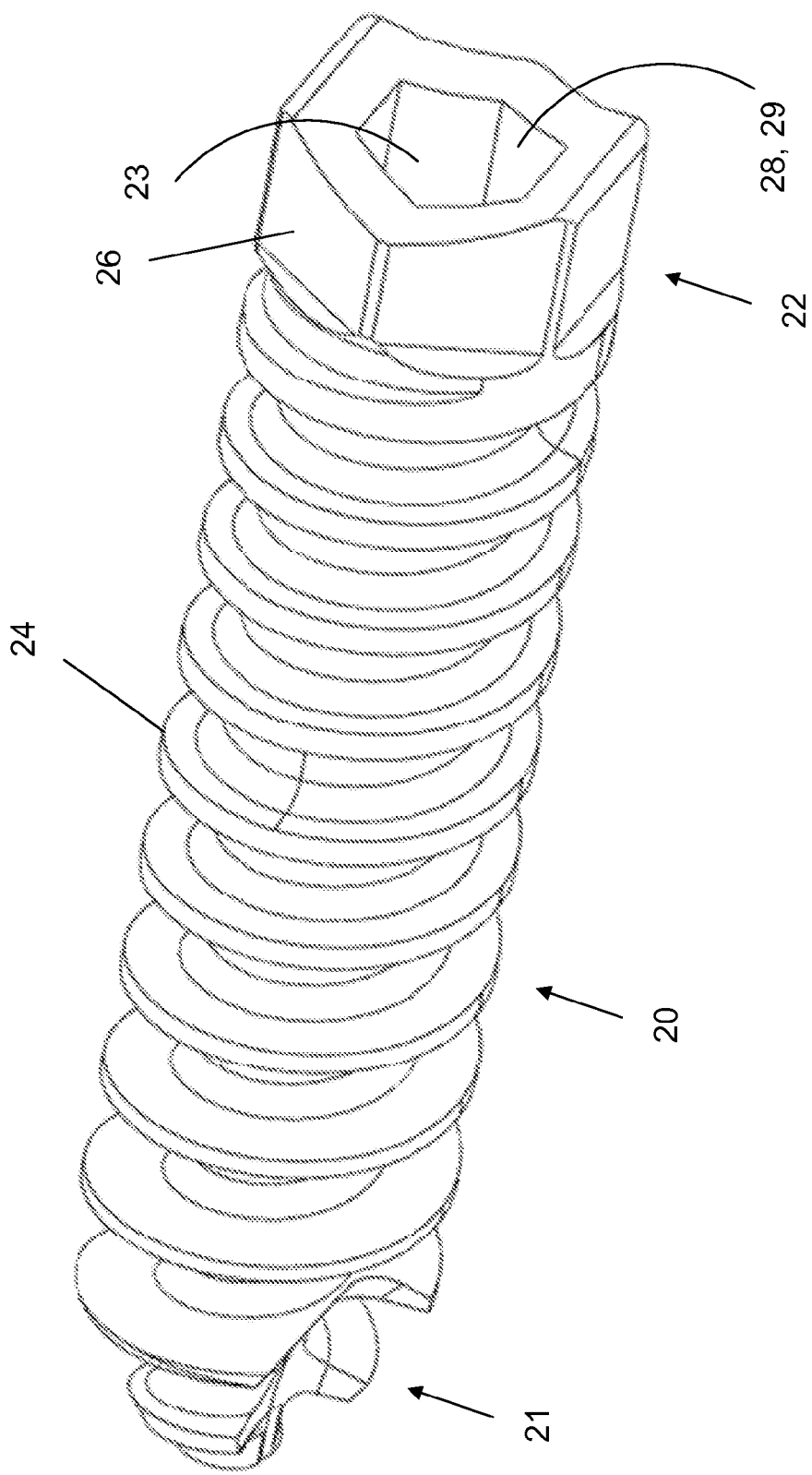
FIG. 13 is a perspective view of one embodiment of the female component of the invention bone joining device.
Figure 14:
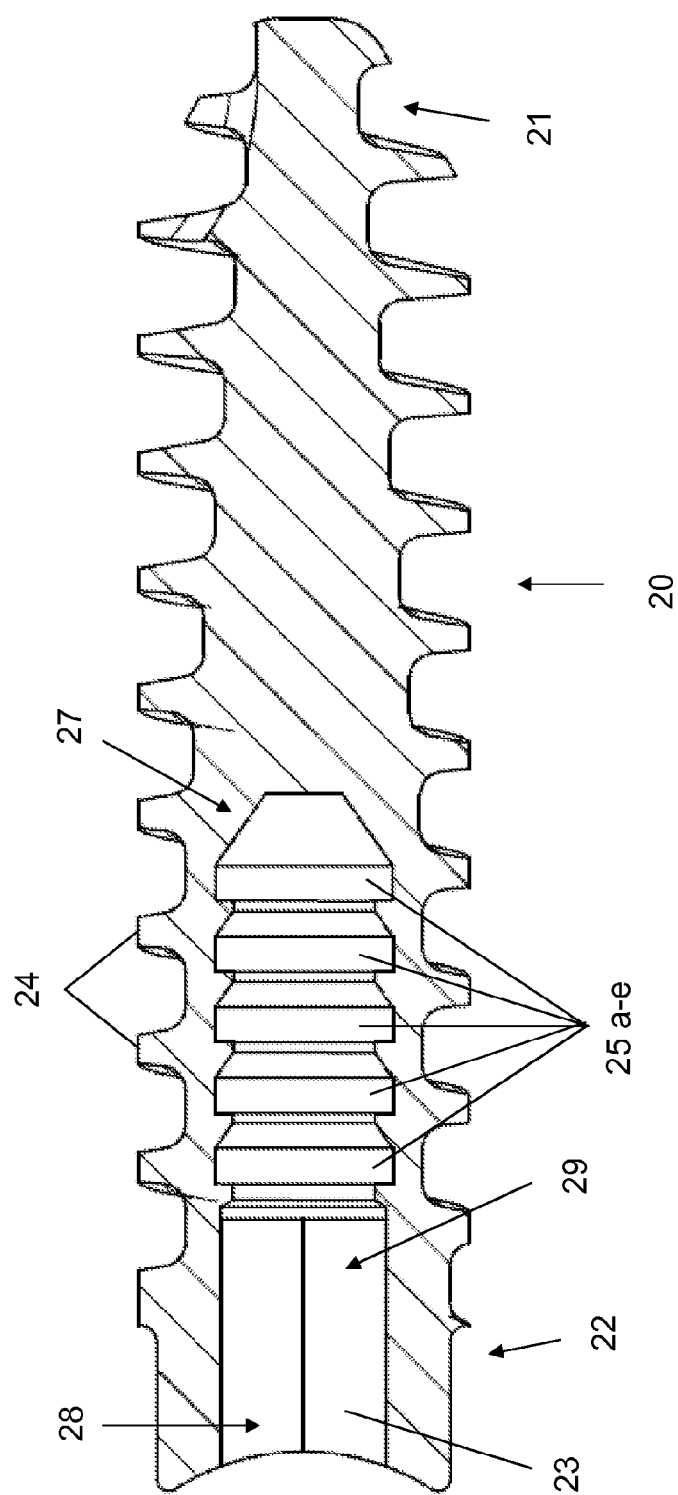
FIG. 14 is a sectional view of one embodiment of the female component of the invention bone joining device.
Figure 15:
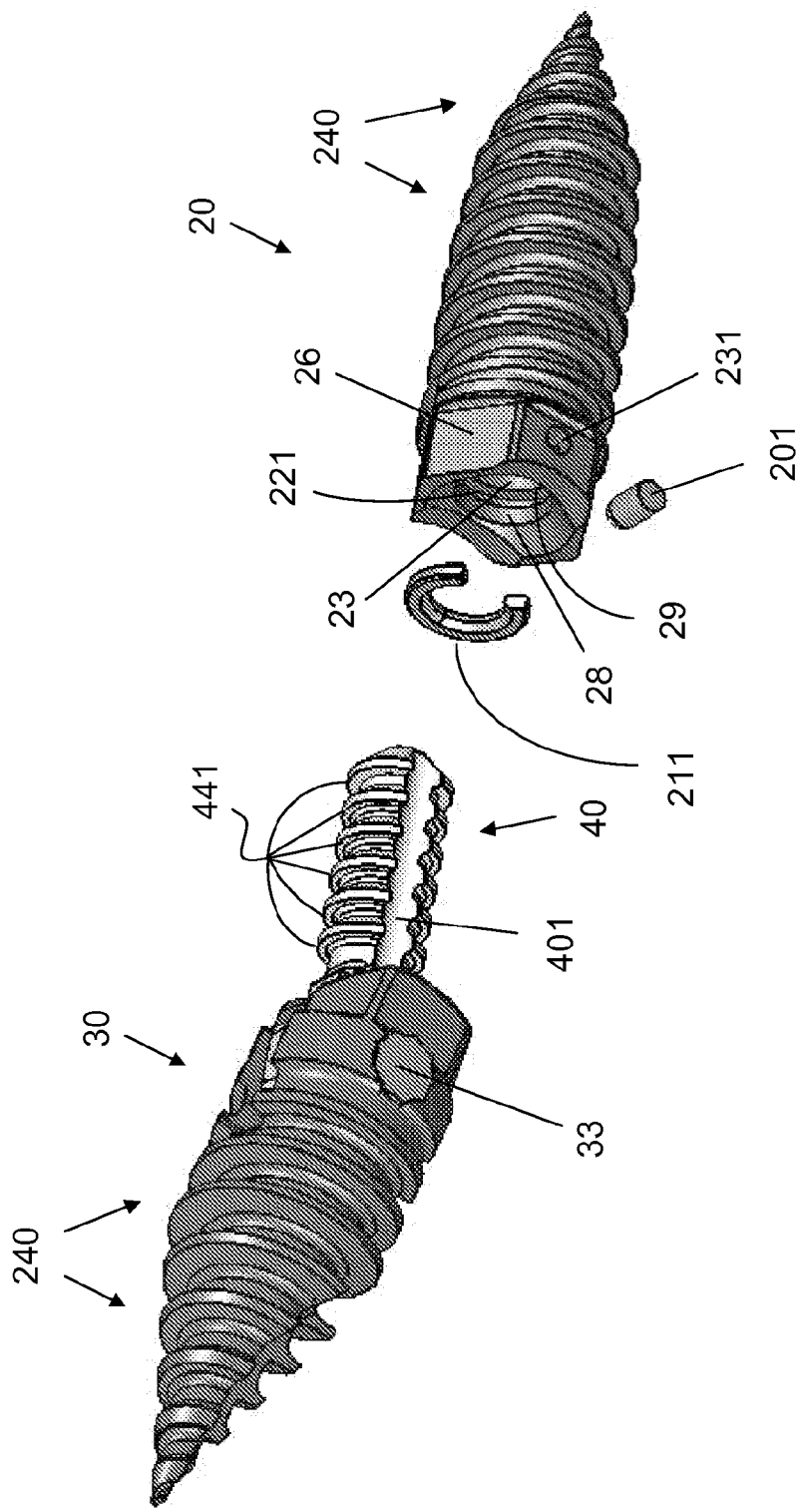
FIG. 15 is an exploded perspective view of one embodiment of the invention bone joining device.
Figure 16:
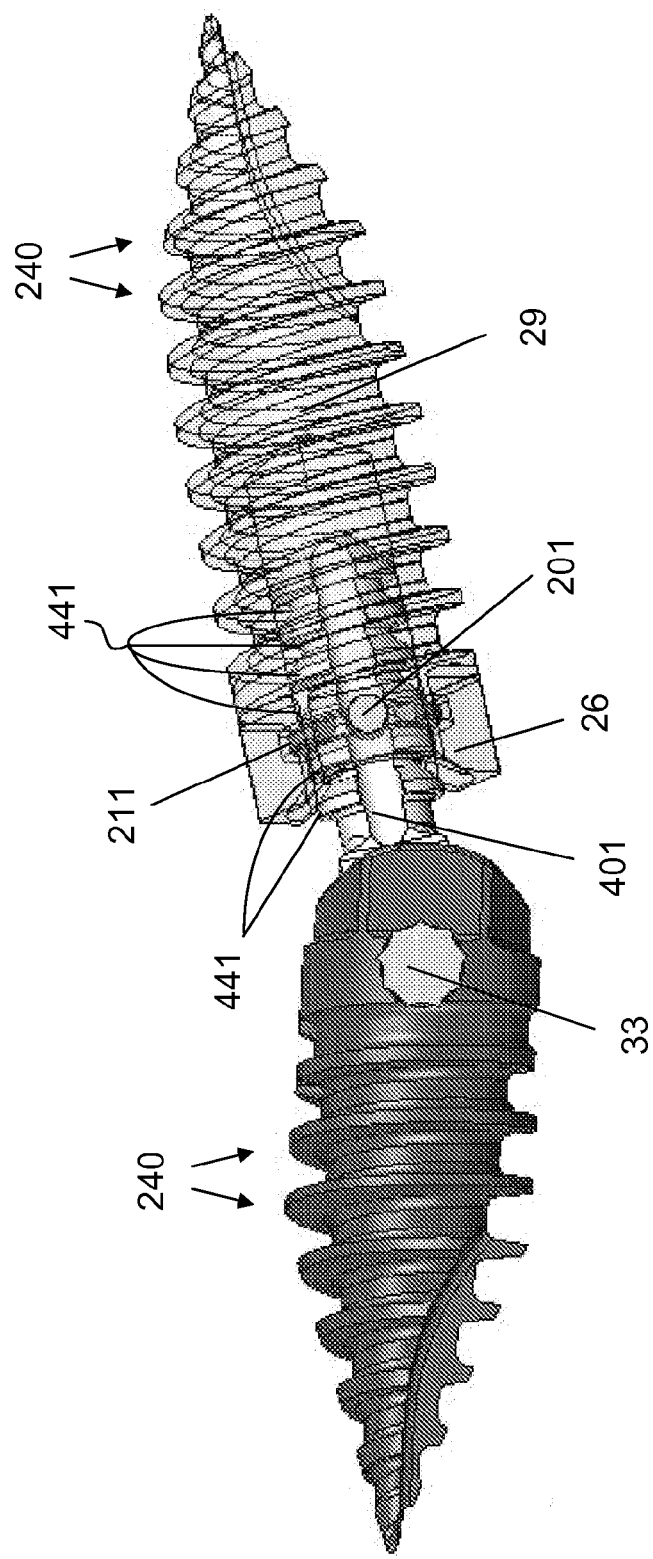
FIG. 16 is a perspective, partial see-through view of one embodiment of the invention bone joining device after partial insertion of the connector into the female component.
Figure 17:
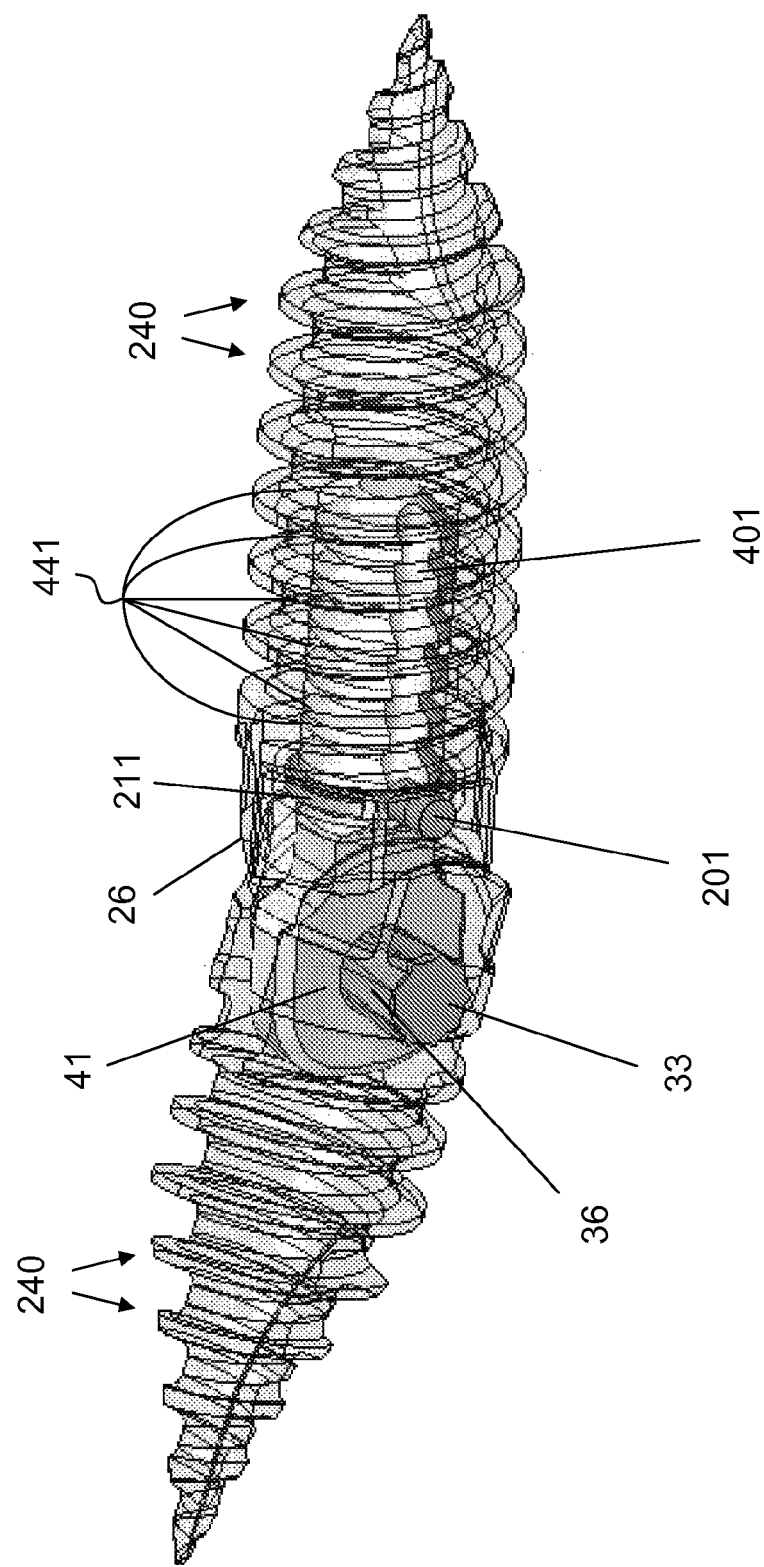
FIG. 17 is a perspective, see-through view of one embodiment of the invention bone joining device after full insertion of the connector into the female component.
Figure 18:
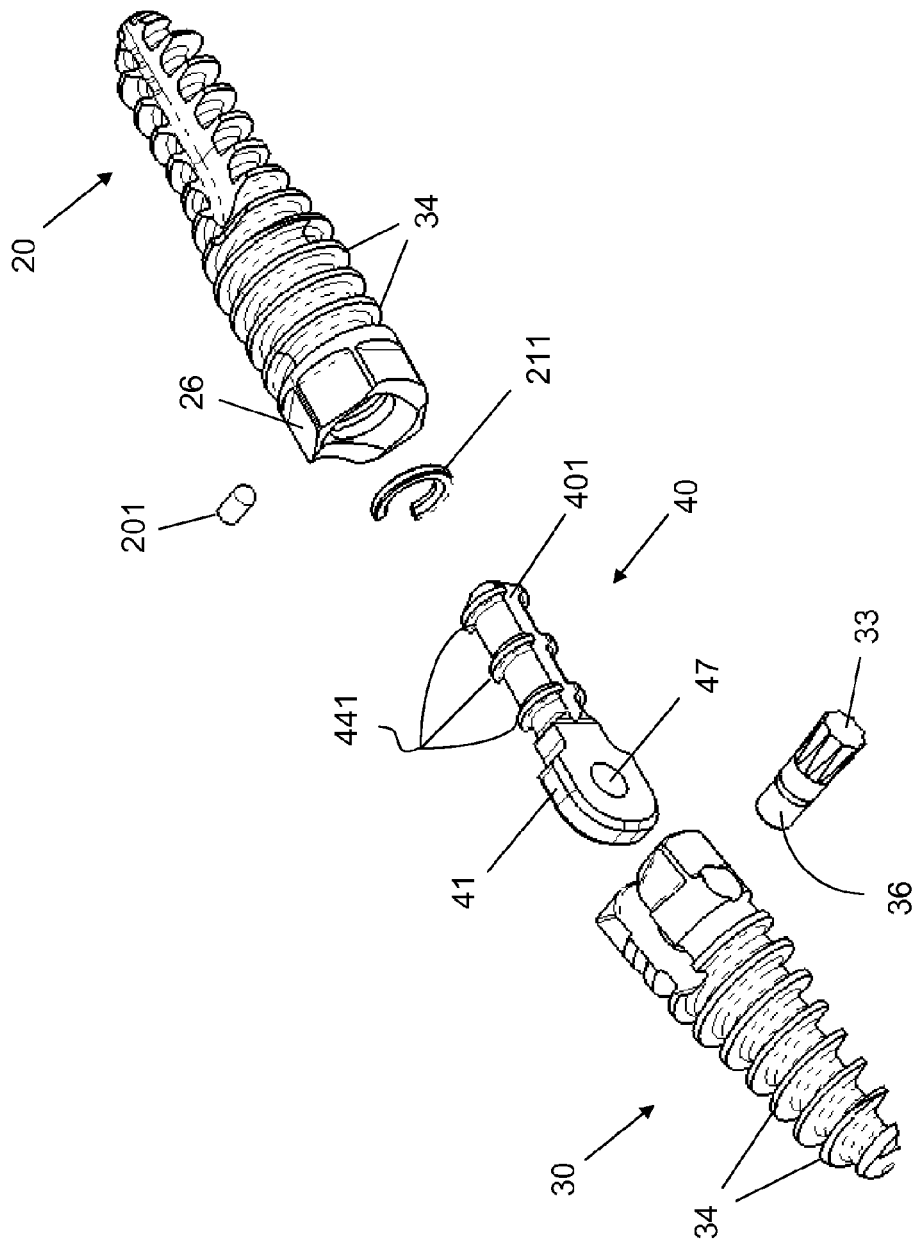
FIG. 18 is an exploded perspective view of one embodiment of the invention bone joining device.

In some embodiments, the cylindrical cavity 29 of the female component 20 is designed to receive the connector 40 through the proximal end 28 of the cavity 29 (FIGS. 13 and 14). In these embodiments, the connector 40 is elongated and cylindrical. The connector further comprises a ring 44 formed around the distal end 42, where the ring 44 has a diameter larger than the diameter of the cylindrical cavity 23 and cross slits 43 directed axially from the distal end 42 toward the proximal end 41 of the connector 40, thereby forming a spring collet 45 (shown in FIGS. 1, 2, 4, 9, 11 and 12).

To accommodate the connector 40 in these embodiments, the cylindrical cavity 29 further comprises at least a first ring-shaped recess 25a circumscribing the cylindrical wall 23 near the distal end such that, when the connector 40 is inserted into the cylindrical cavity 29, the spring collet 45 is compressed until the ring 44 encounters the first recess 25a, where the first recess 25a accommodates a less compressed diameter of the ring 44 and the spring collet 45 transitions to a less compressed state. FIGS. 3-7 show the illustrated embodiment at that position.

To prevent the connector 40 from being pulled out of the cylindrical cavity 29, the ring 44 can comprise an edge 48 on the side closer to the proximal end 41 of the connector 40, where the edge is designed to prevent movement of the connector 40 in the proximal direction after encountering the ring-shaped recess 25a. In the illustrated embodiment, the edge 48 is substantially perpendicular to the wall 23 of the cylindrical cavity 29. In other embodiments, the edge 48 forms an acute angle with the perimeter of the connector 40.

In the illustrated embodiment, the wall 23 of the cylindrical cavity 29 further comprises a second ring-shaped recess 25b circumscribing the cylindrical wall 23 closer to the distal end 27 than the first recess 25a, where the connector 40 can be inserted beyond the first recess 25a, compressing the spring collet 45 until the ring 44 encounters the second recess 25b, where the second recess 25b accommodates a less compressed diameter of the ring 44 and the spring collet 45 transitions to a less compressed state.

The distance between the recesses 25a and 25b in the wall 23 of the cylindrical cavity 29 can be any distance appropriate for the particular application. The distance may be 5 mm or greater, 4 mm, 3 mm, 2 mm, 1 mm, less than 1 mm, or any distance in between these values. In some embodiments, the distance is anywhere from 0.2 mm to 1 mm, for example about 0.6 mm.

In the illustrated embodiment, the wall 23 of the cylindrical cavity 29 further comprises a third ring-shaped recess 25c circumscribing the cylindrical wall 23 closer to the distal end 27 than the second recess 25b, where the connector 40 can be inserted beyond the second recess 25b, compressing the spring collet 45 until the ring 44 encounters the third recess 25c, where the third recess 25c accommodates a less compressed diameter of the ring 44 and the spring collet 45 transitions to a less compressed state.

Figure 8:
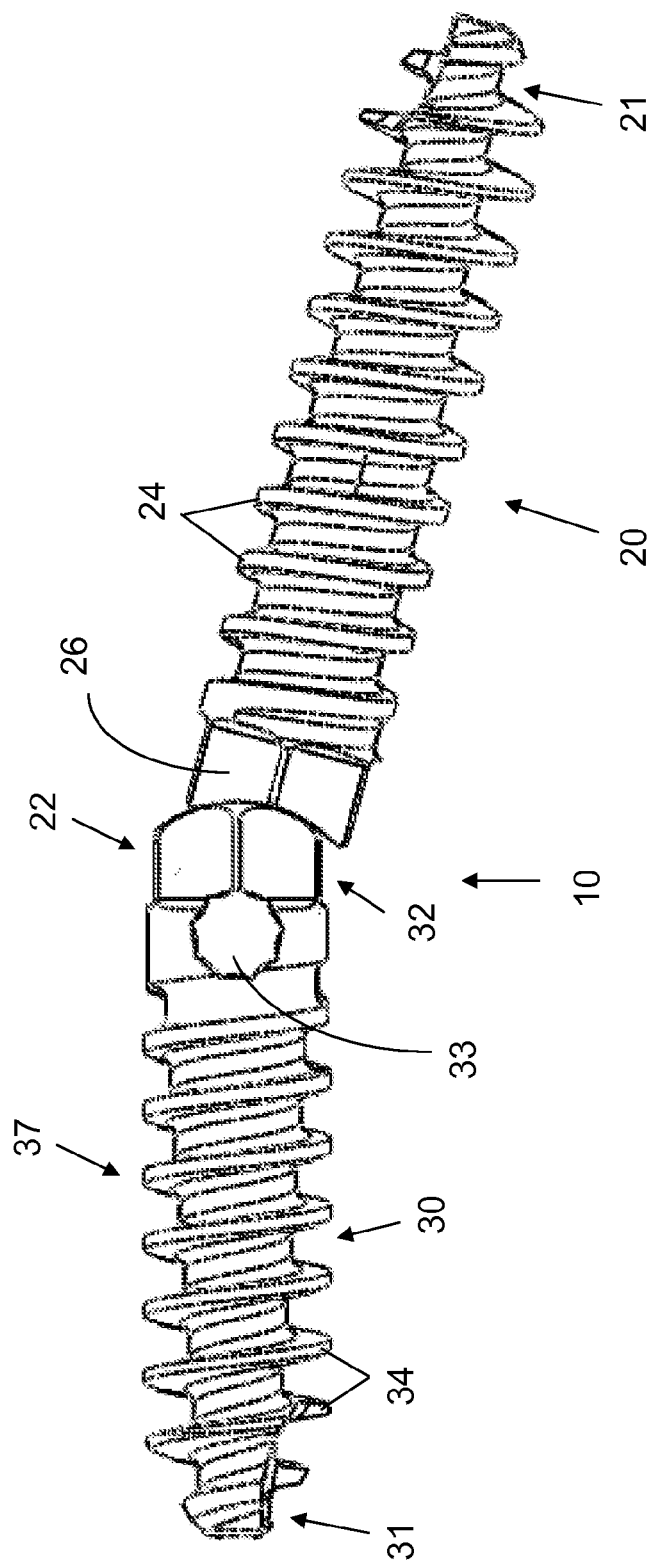
FIG. 8 is a perspective view of one embodiment of the invention bone joining device showing the female component and the male component after full insertion of the connector into the female component.
Figure 9:
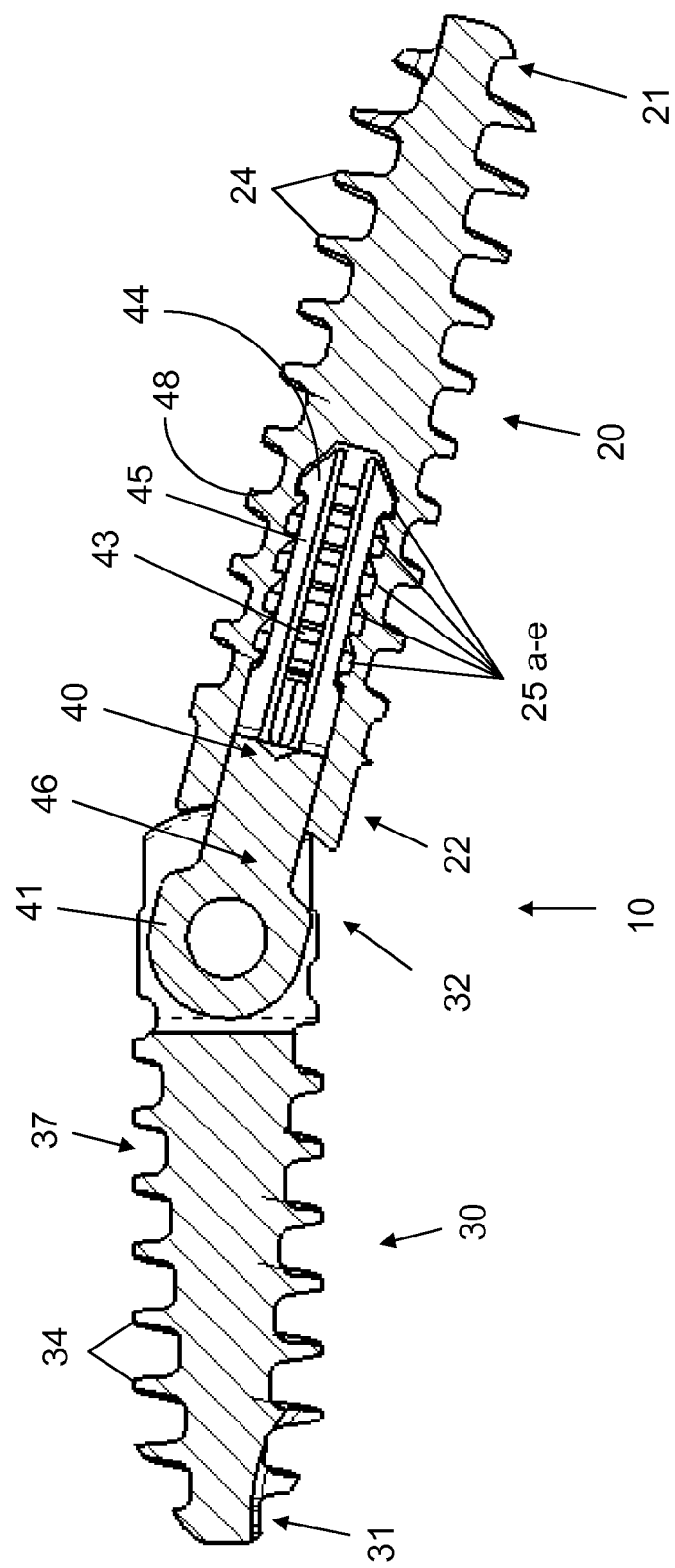
FIG. 9 is a sectional view of one embodiment of the invention bone joining device showing the female component and the male component after full insertion of the connector into the female component.
Figure 10:
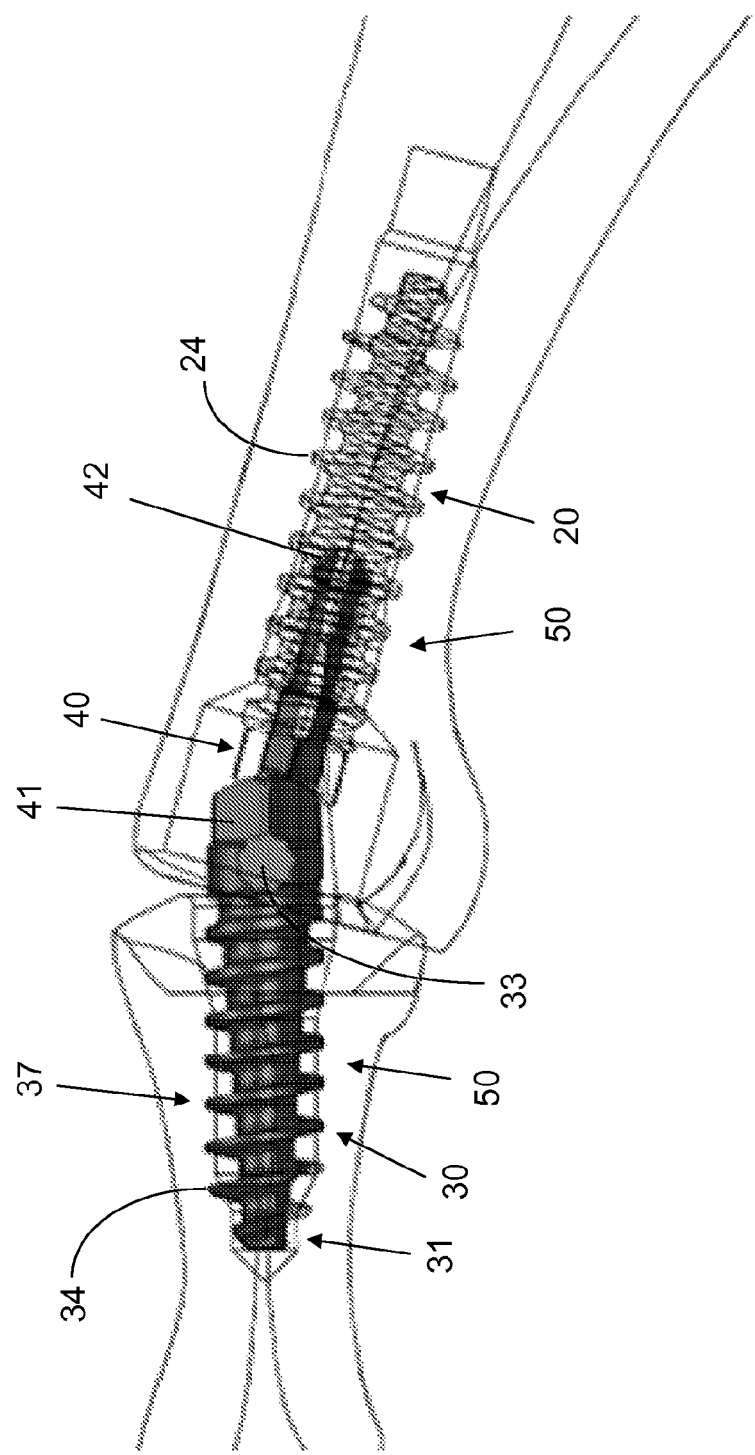
FIG. 10 is a side elevation longitudinal sectional view of a bone with one embodiment of the invention bone joining device in place after full insertion of the connector into the female component.

In the illustrated embodiment, the wall 23 of the cylindrical cavity 29 additionally comprises a fourth and fifth ring-shaped recess 25d and 25e circumscribing the cylindrical wall 23 closer to the distal end 27 than the third recess 25c, where the connector 40 can be inserted beyond the third recess 25c, compressing the spring collet 45 until the ring 44 encounters the fourth recess 25d or fifth recess 25e, where the fourth and fifth recess 25d and 25e accommodates a less compressed diameter of the ring 44 and the spring collet 45 transitions to a less compressed state. FIGS. 8-10 show the illustrated embodiment in that position.

Figure 3:
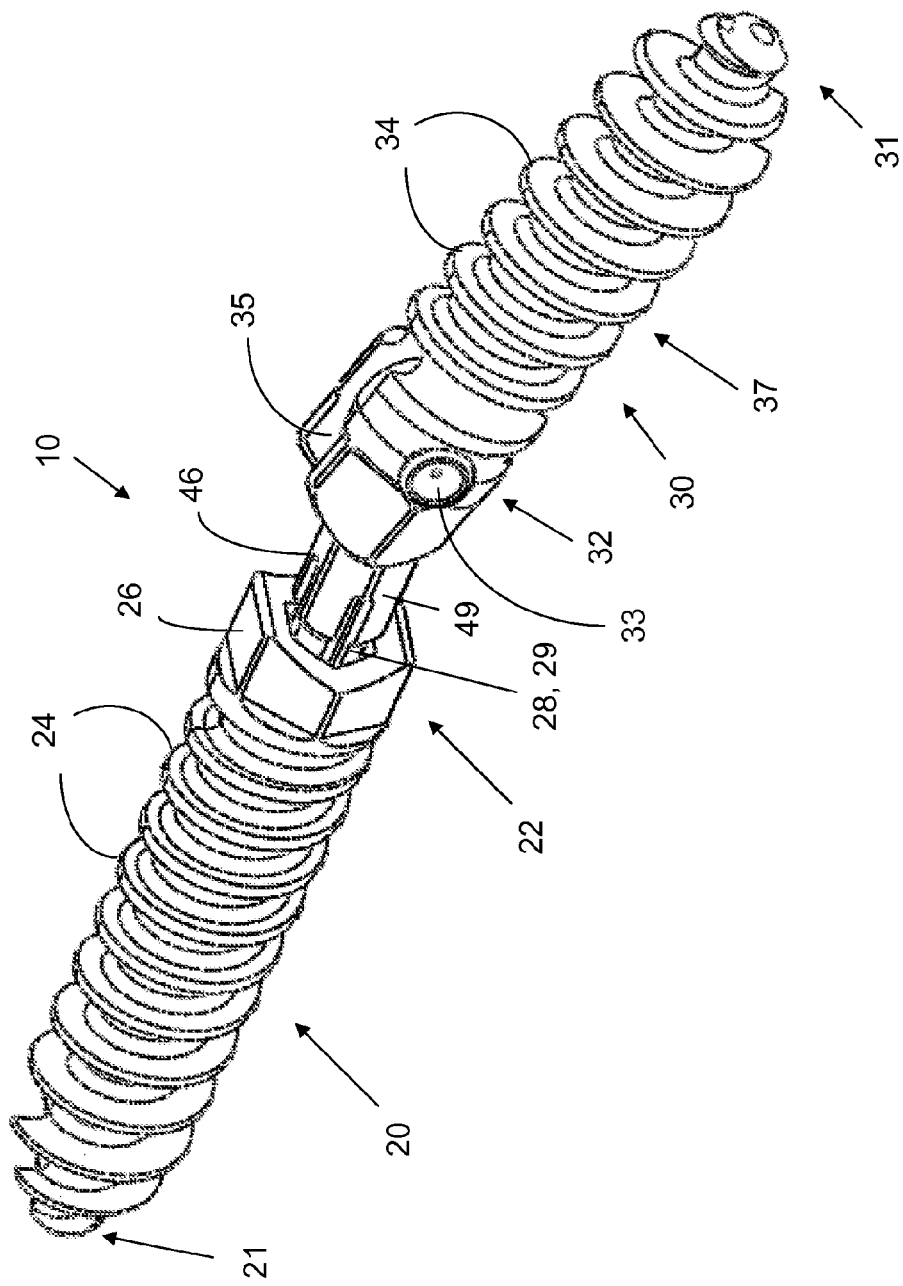
FIG. 3 is a perspective view of one embodiment of the bone joining device after partial insertion of the connector into the female component.
Figure 4:
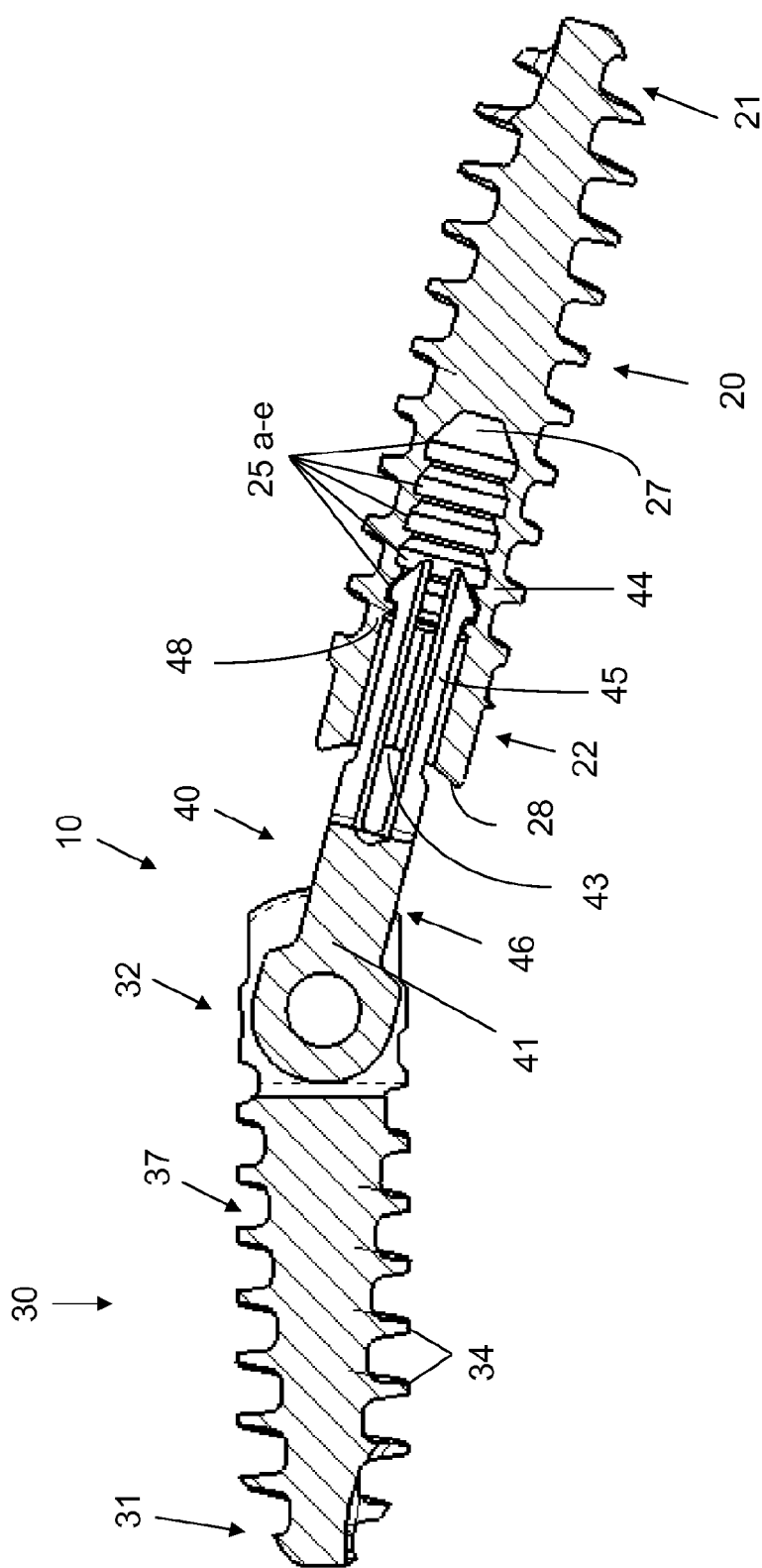
FIG. 4 is a sectional view of one embodiment of the bone joining device after partial insertion of the connector into the female component.
Figure 6:
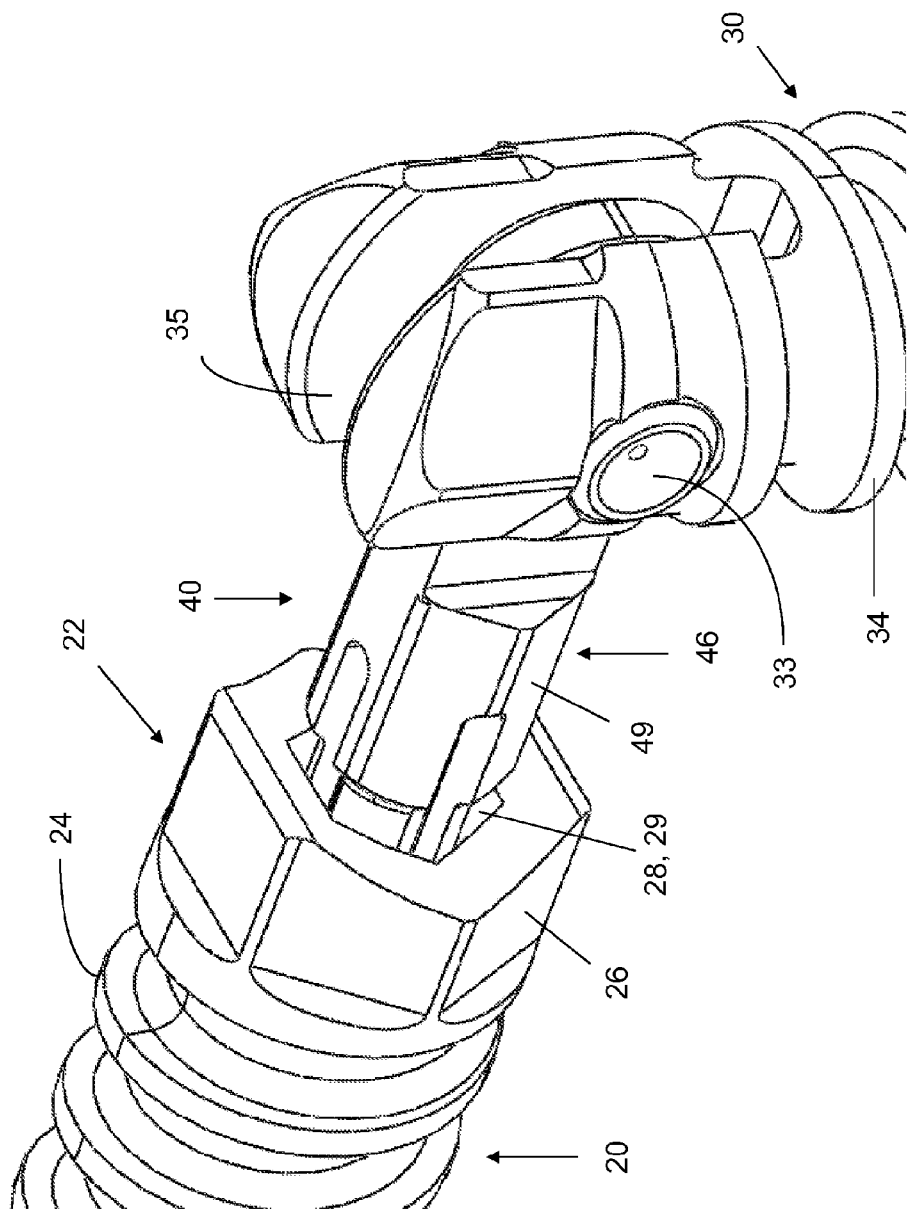
FIG. 6 is an enlarged fragmentary view of one embodiment of the bone joining device after partial insertion of the connector into the female component.
Figure 7:
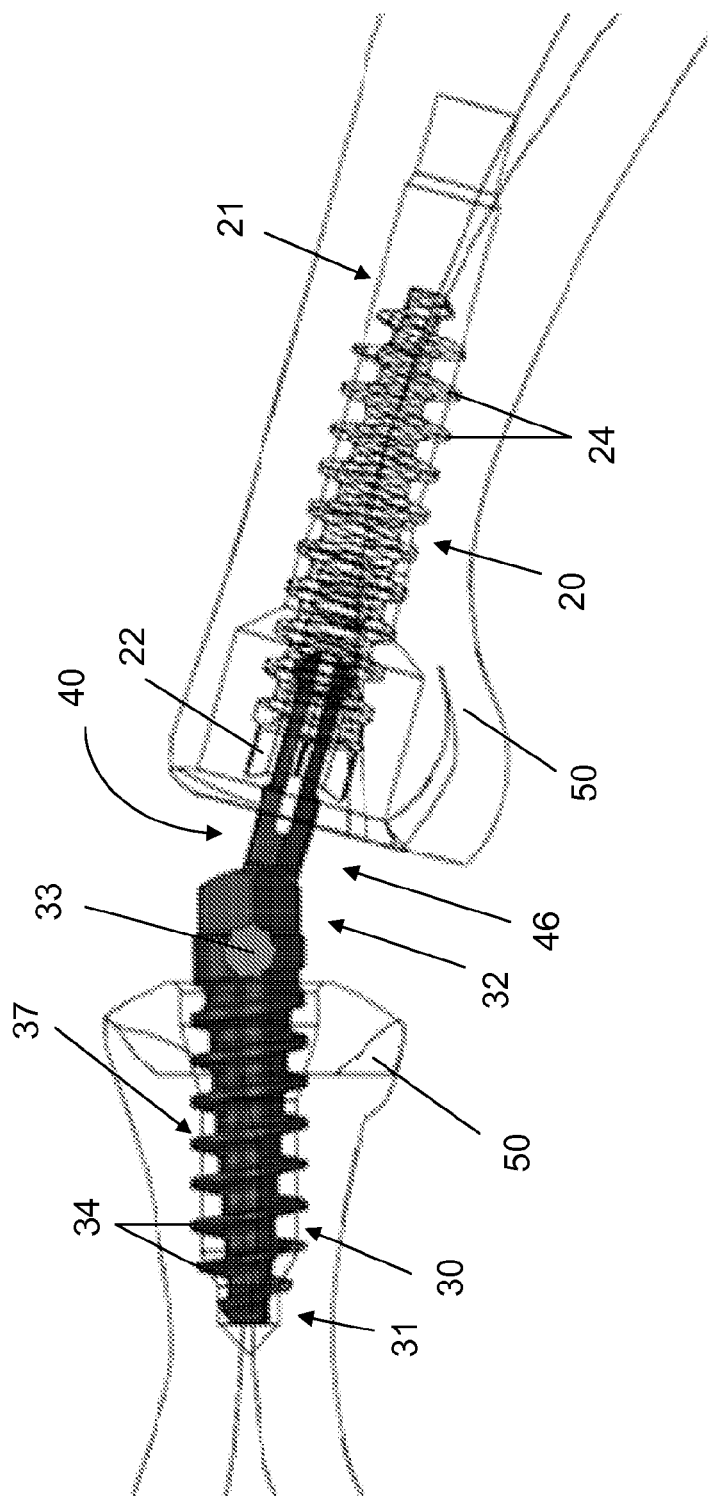
FIG. 7 is a side elevation longitudinal sectional view of a bone with one embodiment of the bone joining device in place after partial insertion of the connector into the female component.

In the operation of the illustrated embodiment, when the connector 40 is inserted into the cylindrical cavity 29 and the spring collet 45 engages the first recess, the connector 40 continues to be capable of being adjustably positioned in relation to the second top 32. This is best illustrated in FIGS. 3, 4 and 6, also showing that when the spring collet 45 is engaged in the first recess 25a, there is a gap between the second top 32 and the first top 22, such that the top of the shaft 46 of the connector 40 is exposed. The gap provides room for the second top to adjustably position the second elongated stem portion 37 to any angle desired. FIG. 7 illustrates the device in a digit, showing the gap between the second top 32 and the first top 22. FIG. 7 also illustrates that, when the spring collet 45 engages the first recess 25a, the device provides continuous adjustability of the male component 30 in relation to the connector 40 in the flexion of the joint. Thus, using the invention device, the joint can be flexed to any degree necessary. If fusion is desired, that fusion can be made at the desired angle of flexion.

In some embodiments, when the female component 20 and the male component 30 are screwed into the bone pieces 50, those two components should rotationally align with each other so that the top of the shaft 46 can fit inside the proximal end of the cylindrical cavity 29. Additionally, when the device is used to fuse a digit, as in e.g., hammertoe treatment, the positioning of the connector 40 in an angular direction should be made in the proper rotational plane, such that the connector 40 can be positioned along an angle that follows the natural flexion of the digit. The identity of the proper alignment of the female and male components can be accomplished by any means, for example by providing marks on the first top 22 and near the proximal end 41 of the connector 40, where the marks align at the desired position of the male component 30 and female component 20 when the ring 44 is in the first recess 25*a*. Additionally, when the ring 44 is in the first recess 25*a*, the connector 40 may be adjusted to the desired angle in relation to the second top 32 and the crimping pins 33 crimped, preventing further angular movement of the connector 40 in relation to the second top 32.

The device may additionally comprise any means to prevent rotation of the connector 40 in relation to the first elongated stem portion 20, and to assure that the male component 30 and female component 20 are properly aligned rotationally. In some embodiments, as illustrated in FIGS. 15-18, the connector 40 comprises a groove 401 along the length of the connector, and the first elongated stem portion 20 further comprises a pin hole 231 through the side of the first elongated stem portion 20, the pin hole 231 further comprising an anti-rotation pin 201 capable of fitting in the groove 401 of the connector 40 when the connector 40 is inserted into the proximal end of the cavity 29 of the first elongated stem portion 20. The anti-rotation pin 201 prevents rotation of the connector 40 in relation to the first elongated stem portion 20 when the anti-rotation pin is in the groove 401 of the connector 40.

In the embodiments illustrated in FIGS. 15-18, the connector 40 further comprises at least two shaft-rings 441 surrounding and protruding from the shaft. Each shaft ring 441 varies from the other shaft-ring(s) in their proximity to the distal end of the shaft. The circumference of the shaft-rings 441 is slightly less than the circumference of the cylindrical cavity 29 in the first elongated stem portion 20 of the female component. Six shaft rings are in the device shown in FIGS. 15-17, and three in the device shown in FIG. 18. The cylindrical cavity 29 in the first elongated stem portion of the female component further comprises a slot 221 circumscribing the cylindrical wall 23 near the proximal end 28 of the cavity 29. The slot 221 further comprises a c-ring 211 fitting therein.

In these embodiments, the c-ring 211 protrudes into the cavity 29 when relaxed. However, the c-ring 221 expands and recedes into the slot 221 when the connector 40 is inserted into the cavity 29 and a shaft-ring 441 encounters the c-ring 221 and pushes against it. This allows the shaft ring 441 to pass the c-ring 221. After the shaft ring 441 passes the c-ring 221, providing space in the cavity 29 to accommodate the relaxed c-ring, the c-ring 221 becomes relaxed again and contracts, re-protruding into the cavity 29. It is envisioned that, after the connector 40 is inserted into the cavity 29 such that the most distal (or second or third most distal) shaft-ring 441 passes the c-ring 221, as in FIG. 16, the connector 40 is manually rotationally adjusted in relation to the male component 30 to the final desired position (e.g., the desired angle of flexion of a joint being fused, or a properly aligned position of the two parts of a broken bone or vertebral fusion). The crimping pin 33 is then crimped, to prevent further rotational movement. The connector 40 may then inserted the rest of the was into the cavity 29, as in FIG. 17, aligning the two bone pieces. It is noted that, in FIG. 17, all six shaft rings 441 have passed the c-ring 221. In the alternate design illustrated in FIG. 18, there are three shaft rings 441.

In the illustrated embodiments, the top of the shaft 46 of the connector 40 comprises a hexagonal formation 49 and the first top 22 comprises a hexagonal recess 26, where the hexagonal formation 49 fits into the hexagonal recess 26 when the connector 40 is inserted into the cylindrical cavity 29. In other embodiments, the formation and recess can be circular, pentagonal, square or any other shape.

Figure 5:
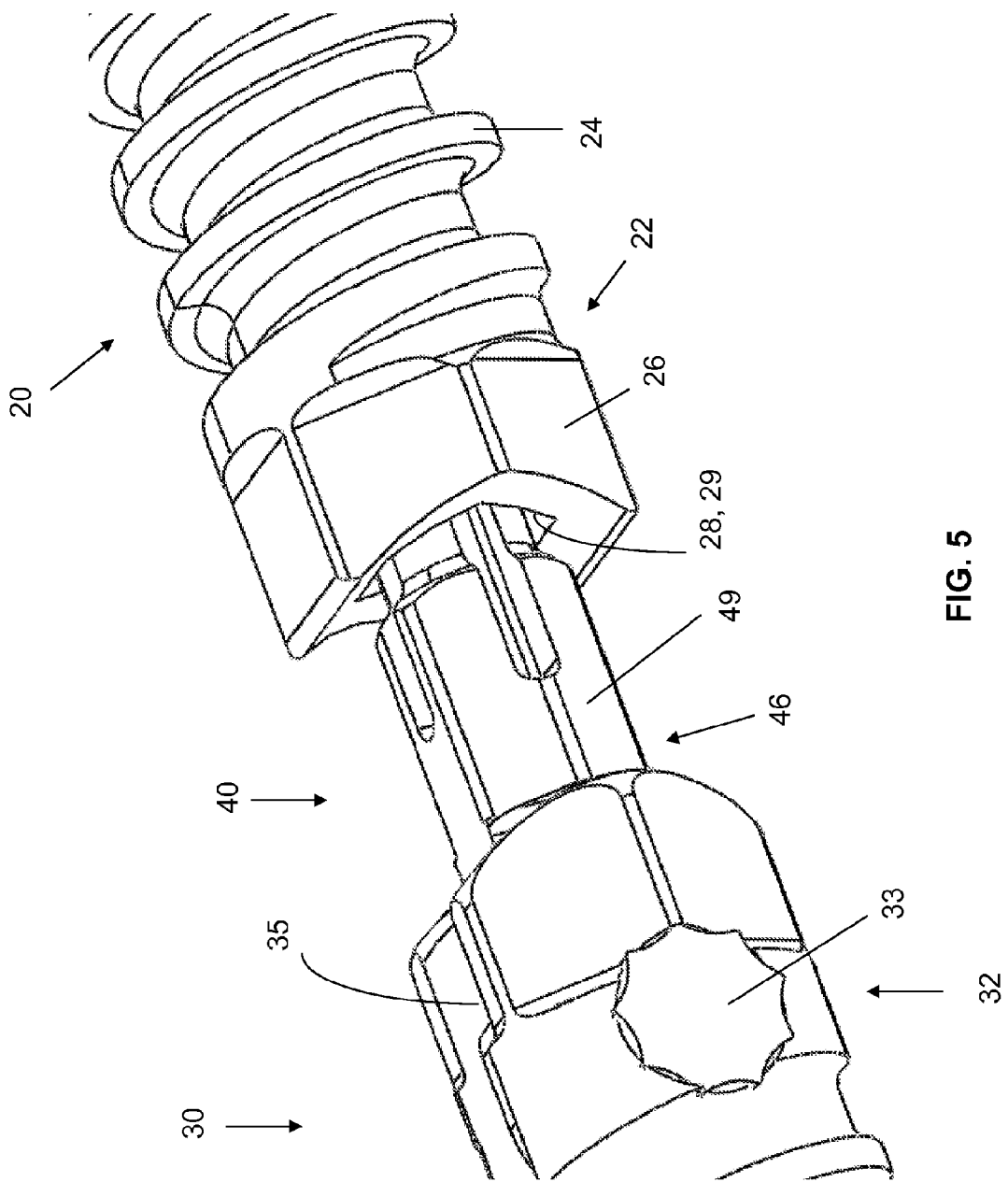
FIG. 5 is an enlarged fragmentary view of one embodiment of the bone joining device after partial insertion of the connector into the female component.

In some embodiments, the first top 22 is concave and the second top 32 is convex, as shown, e.g., in FIG. 5, such that, when screwed into the bones, the first top 22 and the second top 32 match common osteotomy cuts where one bone is cut in a concave shape and the other bone is cut in a convex shape.

In some embodiments, at least one of the hexagonal recess 26 and the hexagonal formation 49 is smoothed where the connector 40 first encounters the hexagonal recess 26 such that the hexagonal formation 49 will fit into the hexagonal recess 46 even if the marks are not fully aligned at the desired position.

Figure 21:
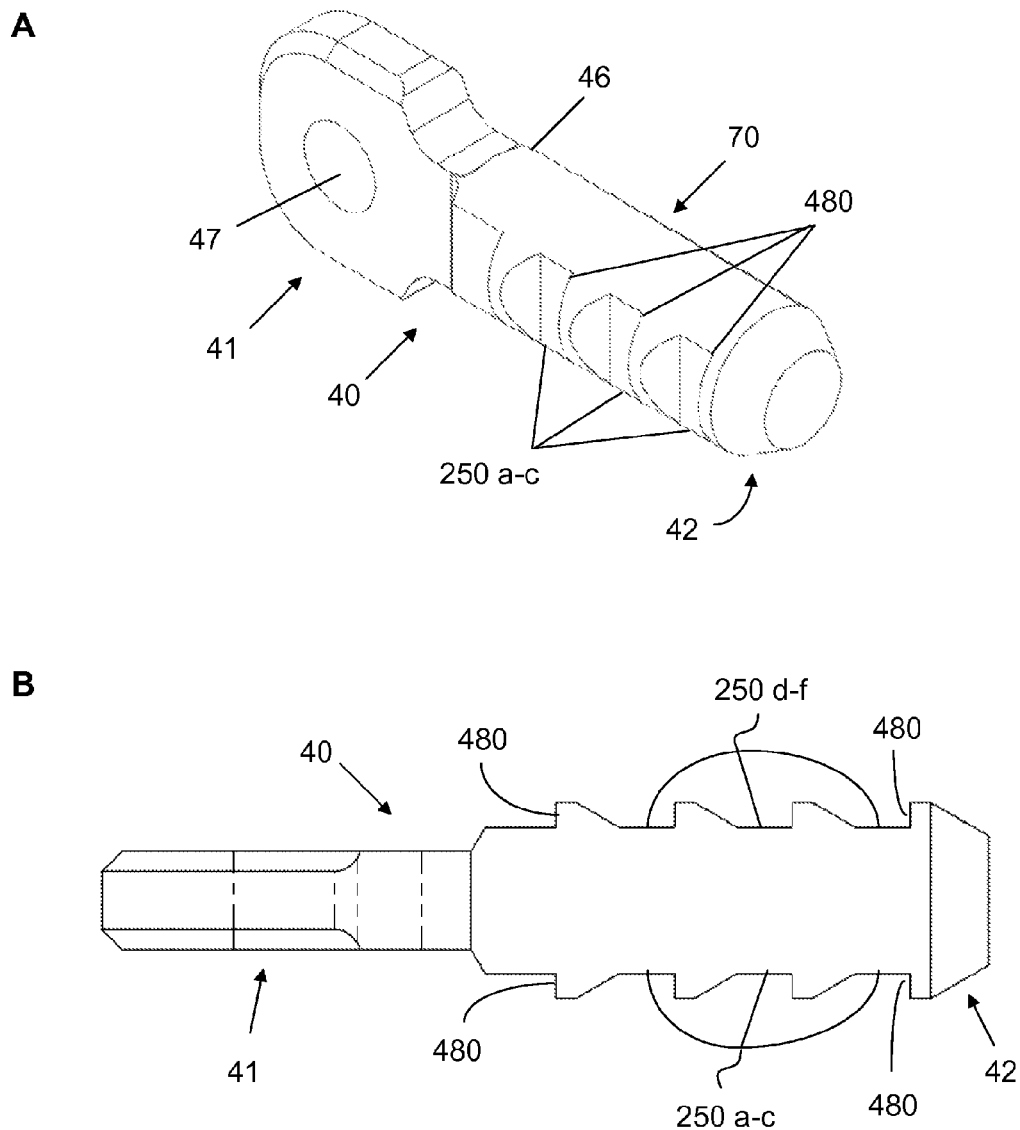
FIG. 21 is a perspective (Panel A) and a cross-sectional (Panel B) view of one embodiment of a connector of the invention bone joining device.
Figure 22:
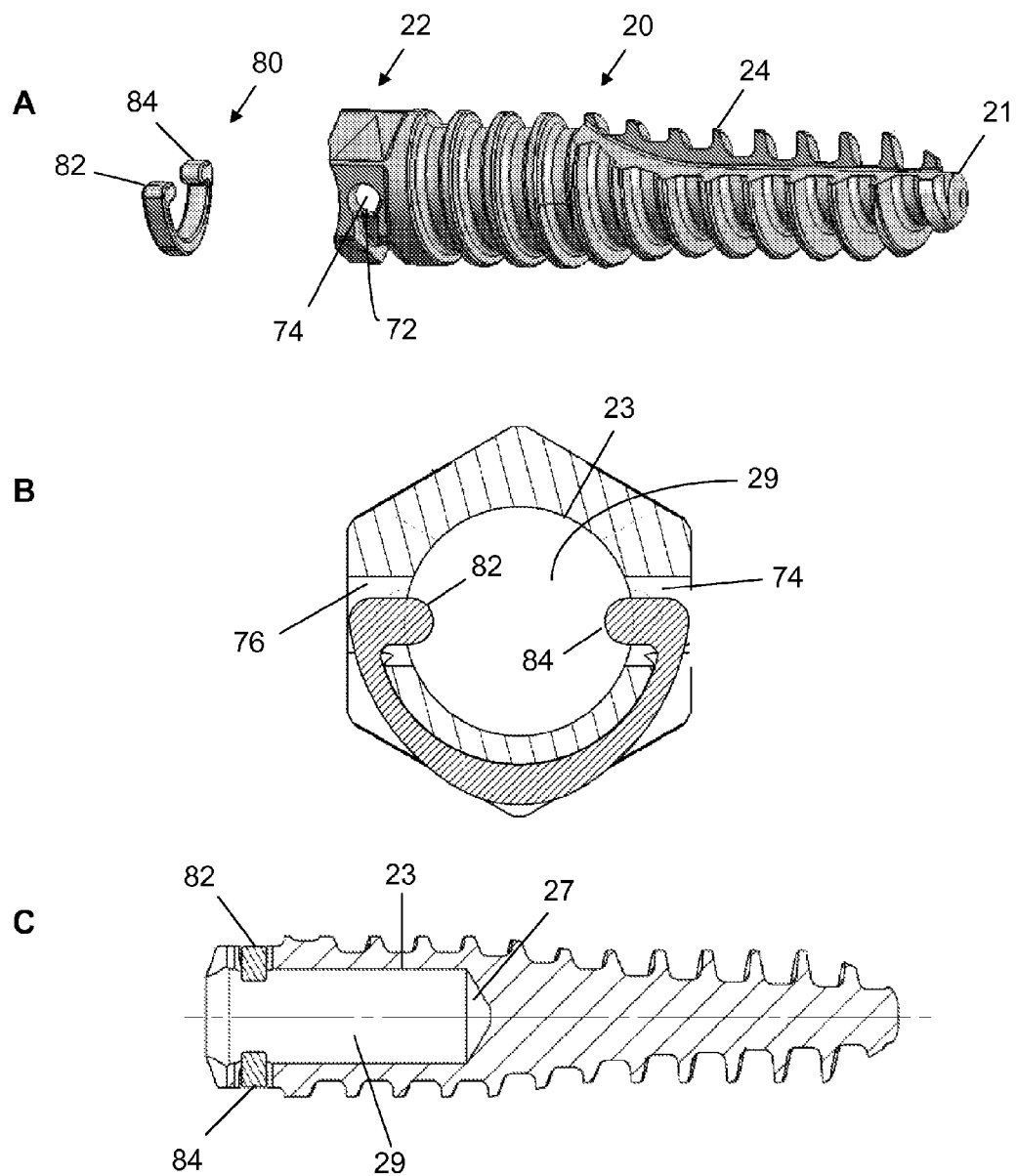
FIG. 22 is a perspective (Panel A) and two cross-sectional (Panels B and C) view of one embodiment of a female component of the invention bone joining device.
Figure 23:
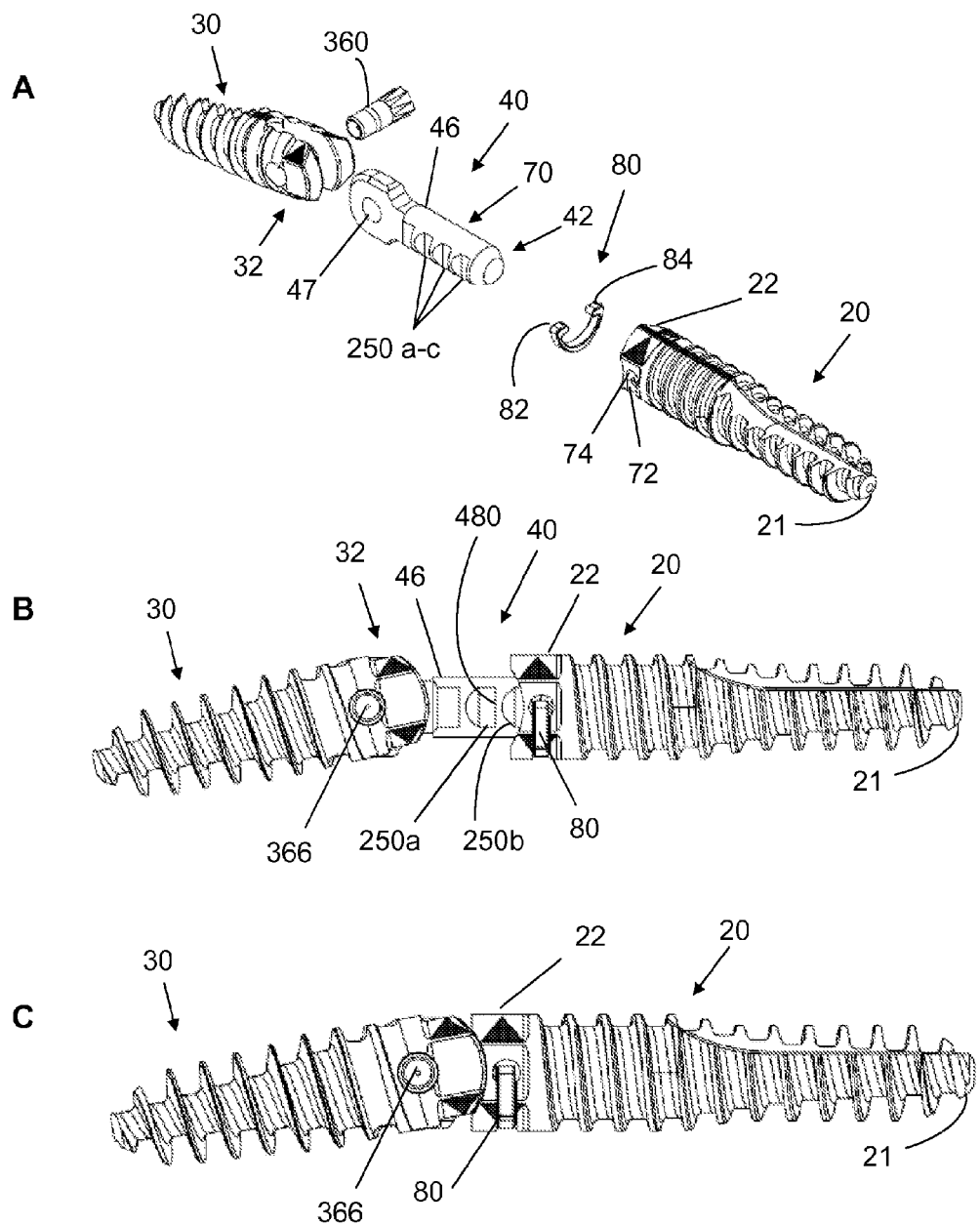
FIG. 23 are three perspective views of one embodiment of the invention bone joining device.

An alternative configuration of the bone fixation device is illustrated in FIGS. 21-23. As in the embodiments described above and illustrated in FIG. 21, the connector 40 of this configuration comprises a proximal end 41 having a connector hole 47, a top of shaft 46 near the proximal end 41, and a distal end 42. In this alternative configuration, the shaft 70 of the connector 40 is cylindrical, with a plurality (here, three) of axially deposed indentations 250*a-c*, 252*a-c* on at least one side of the shaft 70. In various embodiments, the connector 40 may be elongate but not cylindrical, e.g., key-shaped, having a plurality of axially deposed ridges, such as, for example, semicircular, or arced ridges. For the embodiments illustrated in FIGS. 21-23, the cylindrical shaft 70 of the connector 40 comprises a second set of three axially deposed indentations 250*a-c*, 252*a-c* on opposing sides of the shaft.

As shown in FIG. 22, the female component 20 of this embodiment is an elongated stem, comprising a first end 21, a first top 22, an open proximal end 28 and a cylindrical cavity 29. The cylindrical cavity 29 comprises a cylindrical wall 23, a closed distal end 27 and an open proximal end 28. The illustrated female component 20 also comprises a spiraling thread 24 on the exterior of the component, suitable for screwing the component into a bone.

The female component 20 also comprises an indentation 72 at least partially circumscribing the first top 22, with at least one (here, two) hole 74, 76 passing through the first top 22 into the cylindrical cavity 29.

The female component 20 additionally comprises a knobbed c-ring 80, comprising at least one (here, two) knob protruding inward 82, 84. The knobbed c-ring 80 is configured to fit into the indentation 72 in the first top 22 of the female component 20, such that the knobs fit into the holes 74, 76 and protrude into the cylindrical cavity 29.

In use (FIG. 23), the connector 40 is joined to the male component 30 at the connector hole 47 by inserting the narrow end 362 of the locking pin 360 (as illustrated in FIG. 23) or the crimping shaft 36 and crimping pins 33 (as illustrated in FIG. 12) through the hole on one side of the second top 32 and into the connector hole 47. The shaft 70 of the connector 40 is inserted into the open proximal end 28 and into the cylindrical cavity 29 of the female component 20, where the distal end 42 of the shaft 70 encounters the knobs 82, 84 of the knobbed c-ring 80, which are protruding into the cylindrical cavity 29. As the shaft 70 of the connector 40 is pushed further into the cylindrical cavity 29, the distal end 42 of the shaft 70 pushes on the knobs 82, 84, expanding the knobbed c-ring 80 such that the knobs 82, 84 are pushed out of the cylindrical cavity 29 to accommodate the shaft 70, until the knobs 82, 84 encounter the first indentations 250*c,f*, allowing the knobs to move back into the cylindrical cavity 29 in the space created by the indentations, such that the knobbed c-ring 80 compresses back to its original shape. To prevent the connector 40 from being pulled out of the cylindrical cavity 29, the indentations 250 can comprise an edge 480 on the side closer to the distal end 42 of the connector 40, where the edge is designed to prevent movement of the connector 40 in the proximal direction after encountering the indentation 250. In the illustrated embodiment, the edge 480 is substantially perpendicular to the wall 23 of the cylindrical cavity 29. In other embodiments, the edge 480 forms an acute angle with the perimeter of the shaft 70. When the shaft 70 of the connector 40 continues to be pushed further into the cylindrical cavity 29, the knobbed c-ring 80 again expands as the area between the first indentations 250$c,f$ and the second indentations 250$b,e$ pushes the knobs 82, 84 out of the cylindrical cavity 29, until the knobs 82, 84 encounter the second indentations 250$b,e$. This continues until the knobs 82, 84 are at the indentations most proximal to the male component 30, when the device is seated in its final position. At some point before the device is in its final position, the desired angle of flexion between the connector 40 and the male component 30 is made and set by, e.g., fully engaging the locking pin 360 using the pin locking tool 60, or crimping the crimping pins 33 into the crimping shaft 36 (FIG. 12), as appropriate.

The various steps described above can be performed in any order, i.e., before or after the insertion into either or both bone pieces. It should also be understood that the described embodiments are exemplary, and any appropriate modifications can be made to the devices described above. For example, the knobbed c-ring can instead be an o-ring, and/or can comprise one, or any number of knobs in conjunction with a matching number of aligning sets of axially deposed indentations. Additionally, the knob or knobs can be deposed anywhere along the c-ring, e.g., in the middle of the c-ring, on one or both ends, or between the middle and one or both end. Further, the knobbed c-ring or o-ring can be utilized in conjunction with the connectors described in any of FIGS. 16-18, or any similar connector, instead of the c-ring 211 and anti-rotation pin 201 described previously.

In embodiments where the indentations or ridges do not substantially circumscribe the connector, the presence of the knob in the cavity or the gap between ridges has the advantage of limiting the rotation of the connector in the cavity or the gap between ridges, since the presence of the knob in the cavity or the gap between ridges limits any rotation to the width of the indention or the gap between ridges, unless additional force is applied in rotating the connector to force the knob(s) out of the indentation or the gap between ridges, as described in the following paragraph.

The embodiment illustrated in FIGS. 21-23 has the advantage of being removable. For example, the connector 40 can be separated from the female component 20 by rotating the connector 40 in relation to the female component 20 (which can be achieved after implantation by rotating one bone piece in relation to the other). This causes the knobs 82, 84 to slide out of the indentation or the gap between ridges (e.g., 250$a$ and 250$d$ if fully implanted) and onto the portion of the shaft 70 between the opposing indentations or the gap between ridges (e.g., 250$a$ and 250$d$). The connector 40 can then slide out of the female component 20 along that portion of the shaft 70.

As can be seen from the immediately preceding discussion, the presence of the knob in the indentation or the gap between ridges substantially limits the rotation of the connector in the cavity. However, rotating the connector in relation to the cavity is a means for disconnecting the male and female components of the device. As such, the shape and composition of the indentation or the gap between ridges, the c-ring or o-ring, and the knob(s) can be designed to have a balance between the ease with which the male and female components can be disconnected and the force required to overcome the ability of the knob in the cavity to prevent rotation of the connector in relation to the cavity. For example, coating the indentation or the gap between ridges with, e.g., silicone or Teflon to reduce the friction between the knob and the side of the indentation or the gap between ridges, or smoothing or angling the edge of the indentation or the gap between ridges where the knob encounters the wall of the indentation or the gap between ridges when the connector is rotated, makes separation of the male and female components easier and also makes it easier for the connector to be rotated to overcome the resistance to rotation caused by the presence of the knob in the indentation or the gap between ridges. Conversely, having a relatively long knob protruding into the indentation or the gap between ridges makes separation of the male and female components more difficult and also makes rotating the connector to overcome the resistance to rotation more difficult. The number and location(s) of the knob(s) also affect the ease with which rotating the connector to overcome the resistance to rotation can be achieved. For example, using a c-ring with only one knob (corresponding to only one set of axially deposed indentations or gaps between ridges) makes such rotation easier than using a c-ring with two knobs (corresponding to two sets of indentations or gaps between ridges). Also, deposing the knobs on the end of the c-ring makes overcoming the resistance to rotation easier than deposing the knobs toward the middle of the c-ring, since the c-ring requires greater bending distance and force when the knobs are deposed toward the middle in order for them to be pushed out of the cylindrical cavity. Additionally, the use of a c-ring made of a more flexible material makes overcoming the resistance to rotation easier then using a c-ring made of a less flexible material.

The devices described herein can be of any diameter appropriate for the particular bones being joined, as defined by the widest diameter of the spiraling thread 24, 34 of the female component 20 or the male component 30. In some embodiments, the diameter of either component is more than 5 mm. In other embodiments, the diameter of either component is about 5 mm, about 4 mm, about 3 mm, about 2 mm, about 1 mm, less than 1 mm, or any diameter in between, for example about 2.2 mm.

The bone fixation device can be fabricated from any appropriate material. In some embodiments, the device is not bioabsorbable, since it is anticipated that the device provides stability to the fusion site. Additionally, should the two bones joined by the device fail to fuse, the device would provide essential structural support to keep the two bones together. Nonlimiting examples of materials that could be used to fabricate the device include (a) titanium, (b) an alloy of titanium with about 6% aluminum and about 4% vanadium, (c) nitinol, (d) stainless steel, and (e) a polymer such as poly ethyl ethyl ketone (PEEK).

This application is also directed to a method of joining a first bone piece with a second bone piece in a living vertebrate. The method comprises inserting the above-described bone fixation device between the first bone piece and the second bone piece such that the two bone pieces are securely joined.

The method can be used on any vertebrate species. In some embodiments, the vertebrate is a mammal, for example a human.

In some embodiments, the method comprises preparing the two bone pieces to provide a cut surface on each piece that will be joined to each other; inserting the first elongated stem portion longitudinally into the cut surface of the first bone piece such that the first end is inserted first and the first top is at or slightly below the cut surface of the first bone piece; inserting the second elongated stem portion longitudinally into the cut surface of the second bone piece such that the proximal end of the connector is just above the cut surface of the second bone piece; and inserting the connector into the opening in the first elongated stem portion.

In various embodiments, the connector is coupled to the second top at the proximal end by a coupling allowing the adjustable positioning of the connector in an angular direction in relation to the second top. In these embodiments, the method further comprises adjusting the position of the connector in relation to the second top to form a preferred angle of flexion between the two bone pieces; and further inserting the connector into the first elongated stem portion.

In some embodiments, the position of the connector in relation to the second top can no longer be adjusted after the connector is further inserted into the first elongated stem portion. As previously described, this can be accomplished by providing a crimping pin mechanism, as provided in the illustrated embodiments.

These methods can be used to join or fuse any two bone pieces, for example two vertebrae or two halves of a broken bone. In some embodiments, the bone pieces are (a) two adjoining phalanges; (b) a phalanx and an adjoining metacarpal; (c) a phalanx and an adjoining metatarsal; or (d) bone pieces separated by a fracture or osteotomy of a bone diaphysis. Where the subject is a human, these bones can be in the hand or the foot.

In various embodiments, the bone pieces are in the foot of the mammal. The foot can have any condition for which the treatment involves a bone joining two bone pieces. Examples of such conditions include hammertoe, mallet toe, curly toe, or claw toe. In some embodiments, the interphalangeal, metatarsophalangeal or metacarpophalangeal joint is fused.

In other embodiments, the bone pieces are separated by an osteotomy that shortens the bone, for example a lesser metatarsal. An example of such a procedure that can utilize the instant method is a Weil osteotomy, which shortens a metatarsal to provide an improved metatarsal parabola. In those embodiments, the two bone pieces are from a single metatarsal bone that is subjected to an osteotomy of the diaphysis.

In methods utilizing the illustrated embodiment, the first bone is cut in a convex shape and the second bone is cut in a concave shape. These embodiments are particularly accommodated when the first top 22 of the device is concave and the second top 32 is convex, as shown, e.g., in FIG. 5.

Using the illustrated embodiment, these methods can further comprise procedures wherein the first bone piece and the second bone piece are cut; the bone fixation device 10 is inserted between the first bone piece 50 and the second bone piece 50; the connector 40 is inserted into the cylindrical cavity 29 to the first recess 25a before locking the connector 40, where the connector is locked by crimping the crimping pins 33. FIG. 7 shows the device of the illustrated embodiment after this step. In these methods, the connector 40 is further inserted into the cylindrical cavity 29 at least to the second recess 25b, until the cut surface on the first bone piece and the second bone piece are joined together. FIG. 10 shows the device of the illustrated embodiment after this step.

In these methods, the device can further comprise marks on the first top 22 and near the proximal end 41 of the connector 40, the marks aligning at the desired position of the male component 30 and female component 20 when the connector 40 is inserted into the first elongated stem portion (i.e., the female component) 20. In these embodiments, the first elongated stem portion 20 is inserted into the cut surface of the first bone piece 50 by screwing the first elongated stem portion 20 longitudinally into the cut surface of the first bone piece 50, and the second elongated stem portion 37 is inserted into the cut surface of the second bone piece 50 by screwing the second elongated stem portion 37 longitudinally into the cut surface of the second bone piece, where the mark on the first top 22 and the mark near the proximal end 41 of the connector 40 are adjacent to each other after insertion of the second elongated stem portion 37.

In additional embodiments of these methods, the proximal end 41 of the connector 40 comprises a hexagonal formation 49 and the first top 22 comprises a hexagonal recess 26, wherein the hexagonal formation 49 fits into the hexagonal recess 26 when the connector 41 is inserted into the first stem portion 20, where at least one of the hexagonal formation 49 and hexagonal recess 26 is smoothed where the hexagonal formation 49 first encounters the hexagonal recess 26 such that the hexagonal formation 49 will fit into the hexagonal recess 26 even if the marks are not fully aligned at the desired position; and the cut surface of the first bone comprises a notch to accommodate the hexagonal formation 49.

The various embodiments described above can be implanted using any appropriate tools known in the art. Alternative tools, particularly suited for the above embodiments, and methods of implanting the above bone fixation devices in a digit, exemplified on a lesser toe proximal and middle phalanges, are described below and illustrated in FIGS. 24-33.

In some embodiments, to fuse the proximal and middle phalanges, the interphalangeal joint is exposed and the distal end of the proximal phalanx and the proximal end of the middle phalanx are cut off perpendicular to the long axis of each bone. This creates about a 3 mm gap between the bones. A pilot hole is then drilled, e.g., about 18 mm deep, in the proximal phalanx through the intramedullary canal.

The pilot hole can be drilled using any appropriate pilot drill known in the art. In some embodiments, the pilot hole is drilled with a tool designed especially for the device described above, for example the pilot drill 90 shown in FIG. 24. Such a drill comprises an elongate shank 91 having a proximal end 92 and a distal end 93. The proximal end can comprise a handle or can be configured to join to a separate handle, for example the quick connect handle 160 illustrated in FIG. 34. The distal end 93 terminates in a drill tip 94 comprising at least one spirally deposed flute 95 having a sharp outer edge and terminating in a point 96. In some embodiments, as in FIG. 24, there are two spirally deposed flutes 95. The cutting surface defined by the sharp outer edge has the same diameter as the shank 91. The diameter should be less than the diameter of the spiraling thread 24 of the female component 20, to be implanted therein. In some embodiments, the spiraling thread of the female component 20 is 2.2 mm and the diameter of the shank 91 and spirally deposed flute 94 is 2.0 mm. Some embodiments of the pilot drill 90 further comprise a mark or marks (e.g., laser markings) indicating a distance from the point 96 to provide a guide for determining the depth of the hole to be drilled. For example, the pilot drill 90 illustrated in FIG. 24 has marks 97, 98 at 9 mm and 18 mm.

A 2.0 mm pilot hole can be drilled about 18 mm deep in the proximal phalanx through the intramedullary canal. This can be followed with a reamer to shape the hole to accommodate the female component 20. In some embodiments, the reamer prepares a hole with a widened bore near the top to accommodate the top 22 of the female component, e.g., as illustrated in FIG. 25C. A suitable reamer is illustrated in FIG. 25A. The proximal reamer 100 comprises an elongate first shank 101 having a first proximal end 102 and a first distal end 103. The first proximal end can comprise a handle or can be configured to join to a separate handle, for example the quick connect handle 160 illustrated in FIG. 34. The first distal end 103 terminates in a first shaping drill end 104 terminating in a first point 106. Just proximal to the first point 106 is a plurality of first ridges 105 having sharp edges designed to cut the hole illustrated in FIG. 25C. Proximal to the first ridges is a first short shaft 104, and proximal to the first short shaft 104 is a first shoulder 107, wider than the first short shaft 104 and having the approximate diameter of the first shank 101. Proximal to the first shoulder 107, is a first skirt 108, wider than the first shoulder and having a convex first distal surface 109. The proximal reamer 100 also comprises a first cutout 110, extending from the plurality of first ridges 105, through the first short shaft 104, the first shoulder 107, and the first skirt 108. The first cutout 110 has sharp lateral edges 111 designed to cut through the bone as the proximal reamer 100 is rotated and driven therein.

Figure 29:
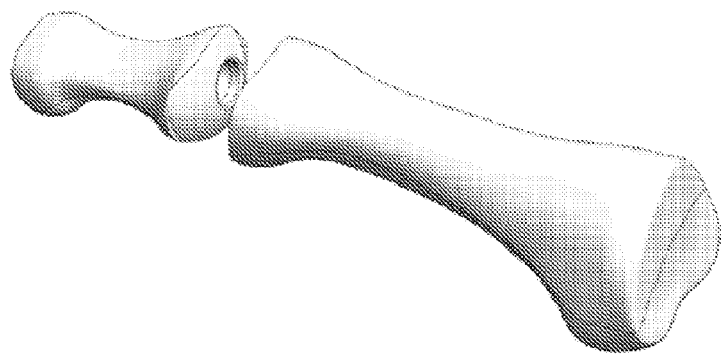
FIG. 29 is perspective views of proximal and middle phalanges of a lesser toe aligned as when the invention bone joining device is inserted therein.
Figure 29:
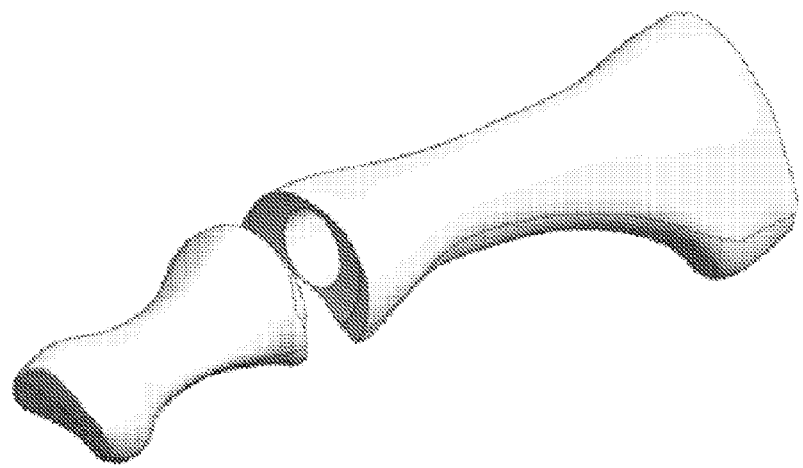
Figure 30:
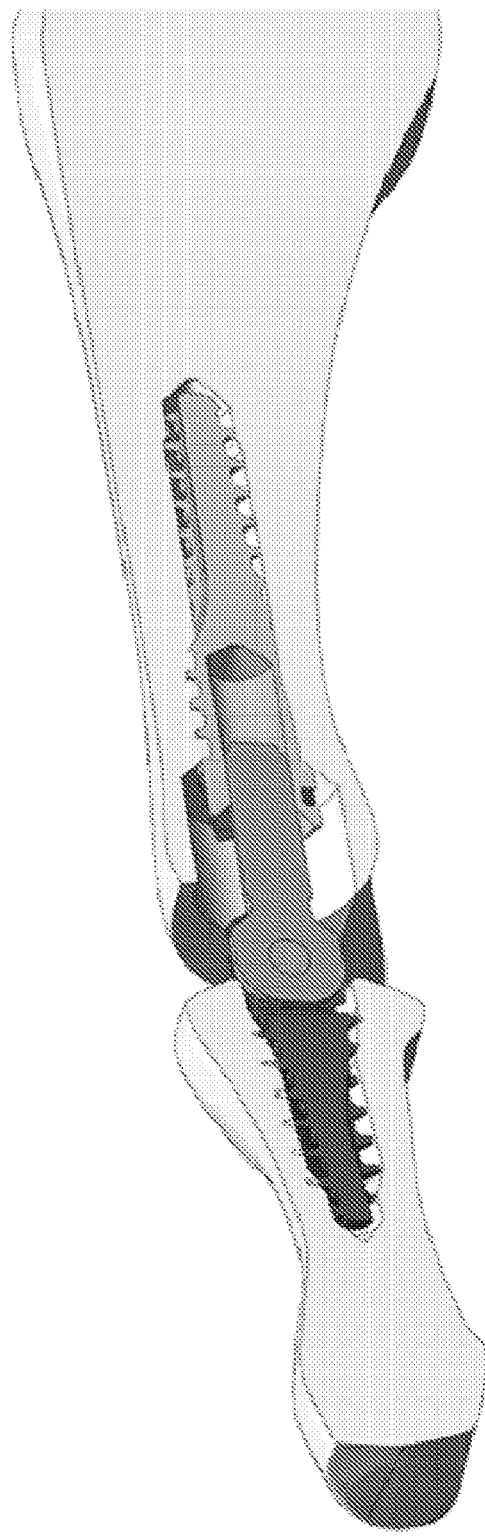
FIG. 30 is a sectional view of the invention bone joining device inserted into proximal and middle phalanges of a lesser toe.
Figure 31:
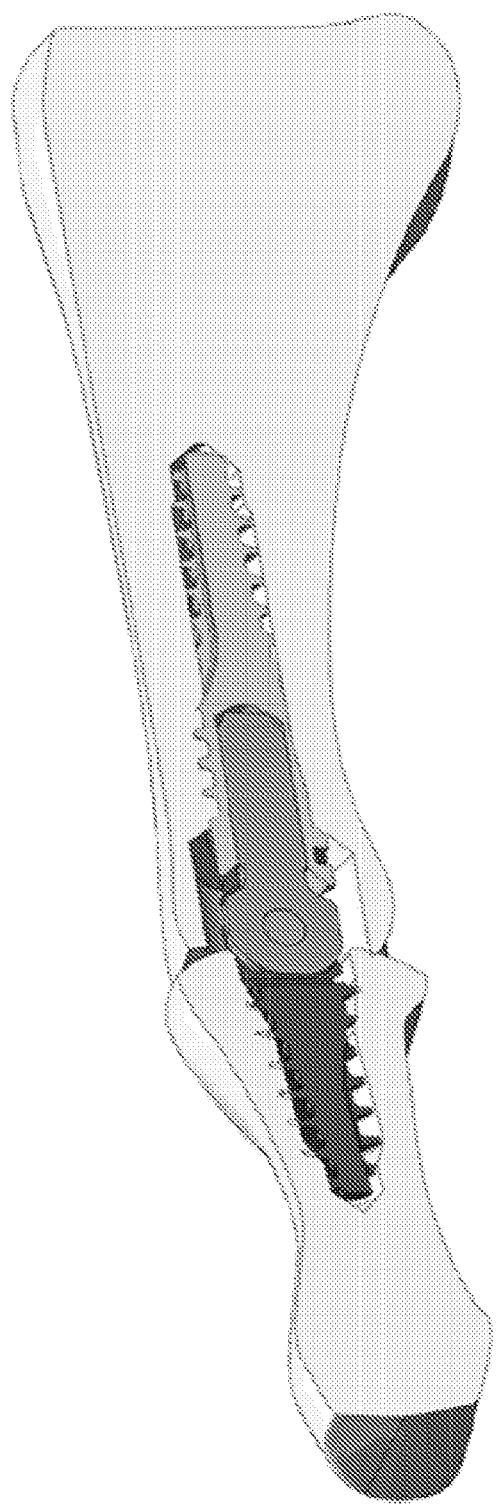
FIG. 31 is a sectional view of the invention bone joining device inserted into proximal and middle phalanges of a lesser toe.

The hole cut by the proximal reamer 100, depicted in FIG. 25C, preferably has a diameter smaller than the diameter of the spiraling thread 24 of the female component 20, such that when the female component 20 is screwed into the hole, the spiraling thread 24 will drive through the intramedullary canal of the phalanx. FIG. 25B shows an example of the alignment of the female component 20 with a suitable proximal reamer 100, where the first ridges 105 and the first short shaft 104 have a diameter of 2.0 mm, while the spiraling thread 24 of the female component 20 has a diameter of 2.2 mm. The proximal reamer 100 also reams a concave surface 112 in the face of the bone, to allow the female component 20 to fit with the male component 30 as depicted in FIG. 29. The wide bore 113 cut by the first shoulder 107 allows the first top 22 to be "buried" in the bone, as shown in FIGS. 30 and 31. The diameter of the concave surface 112 in this example is about 15 mm.

Once the hole in the distal end of the proximal phalanx is prepared, e.g., by the proximal reamer 100, the female component 20 can be inserted. That insertion can be prepared using any suitable tool. A suitable tool for that purpose is the proximal driver 120, partially illustrated in FIG. 26. The proximal driver 120 comprises an elongate first shank 121 having a first proximal end (not shown) and a first distal end 122. The first proximal end can comprise a handle or can be configured to join to a separate handle, for example the quick connect handle 160 illustrated in FIG. 34. The first shank 121 comprises a first slidable bobbin 123. The distal end 122 of the proximal driver 120 comprises two first half sections (not shown) operably linked to the first bobbin 123 such that sliding the first bobbin 123 forward forces these two first half sections together to hold the first top 22 of the female component 20 securely. In some embodiments, the first distal end 122 of the proximal driver 120 comprises a first marking 124 (e.g., a laser marking) that aligns with a first marking 125 on the first top 22 of the female component 20 to easily align the proximal driver 120 with the female component 20.

The first top 22 of the female component 20 is placed in the proximal driver 120 and the first bobbin 123 is slid forwards to securely hold the first top 22. The first top 22 is placed in the driver such that the first marking 124 on the proximal driver 120 lines up with the first marking 125 on the first top 22. The female component is then screwed into the proximal phalanx until the distal end 122 of the proximal driver 120 is even with the hole and the first marking is facing upwards. This places the concave surface 112 in the proper position to mate with a convex shape (described below) in the proximal end of the middle phalanx, thus allowing downward flexion of the middle phalanx through movement of the connector 40 in relation to the second top 32 of the male component 30.

In some embodiments, the preparation of the proximal end of the middle phalanx and the insertion of the male component 30 therein proceeds similar to the insertion of the female component 20 into the distal end of the proximal phalanx described above.

Figure 24:
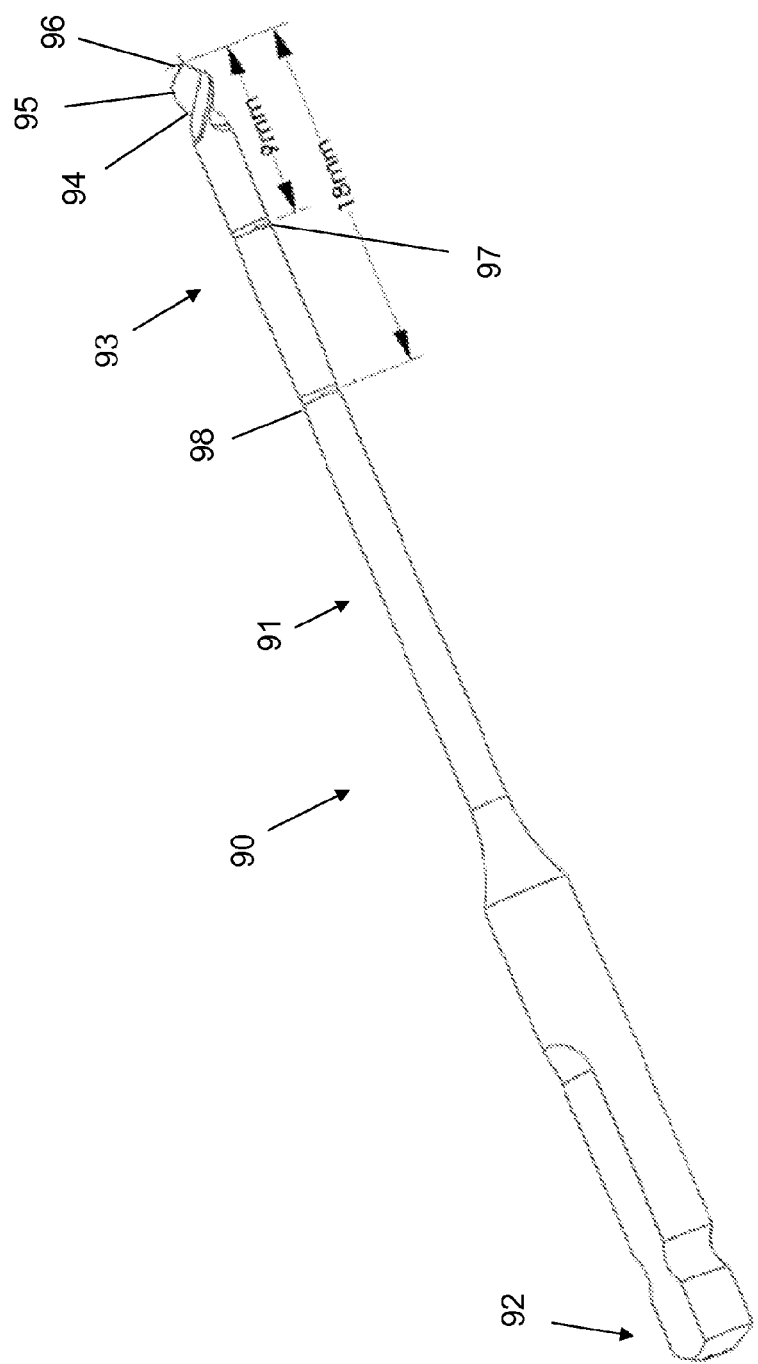
FIG. 24 is a perspective view of a pilot hole drilling device of one embodiment of the invention bone joining device.
Figure 25:
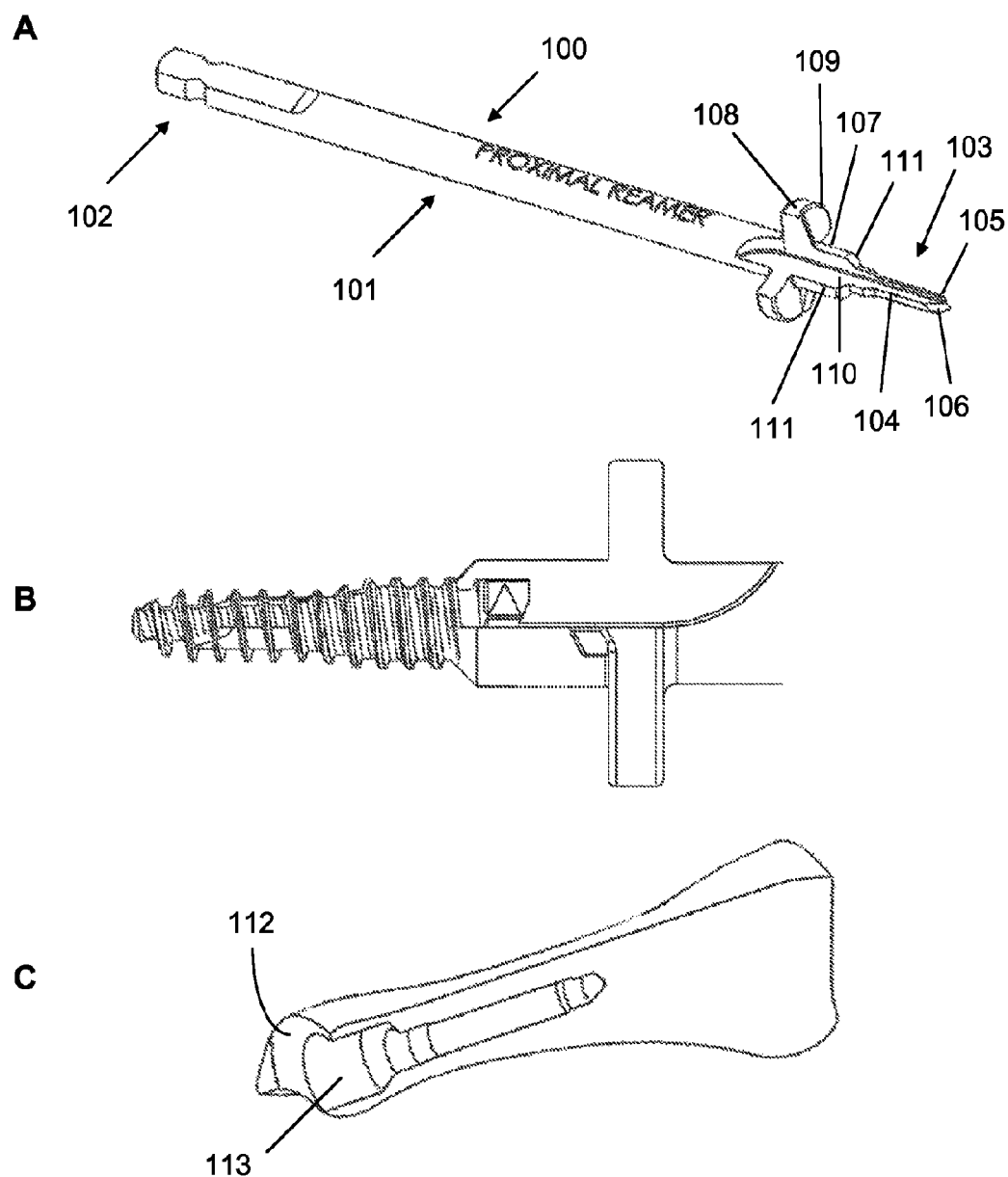
FIG. 25 is a perspective view of one embodiment of a proximal reamer (Panel A), a perspective view of the proximal reamer aligned with a female component (Panel B) and a perspective view of a sectioned bone showing a hole drilled by the proximal reamer (Panel C).
Figure 26:
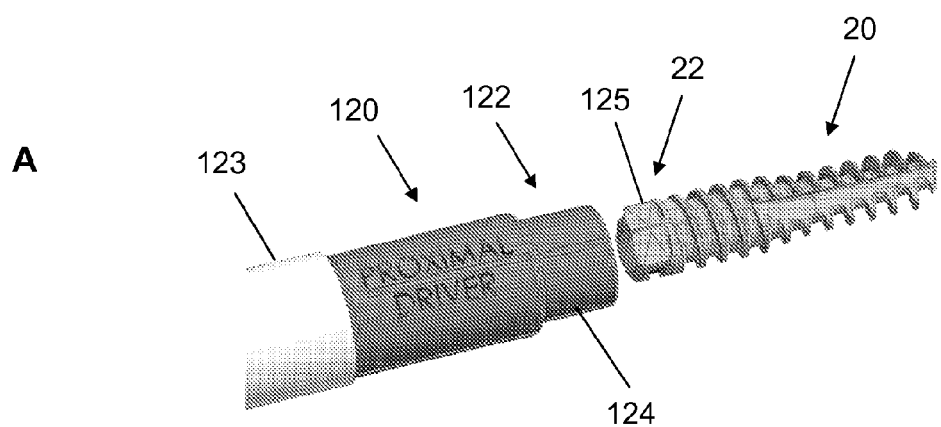
FIG. 26 is a perspective view of a portion of a proximal driver and a female component (Panel A), and a section of the proximal driver and female component inserted into a bone (Panel B).
Figure 26:
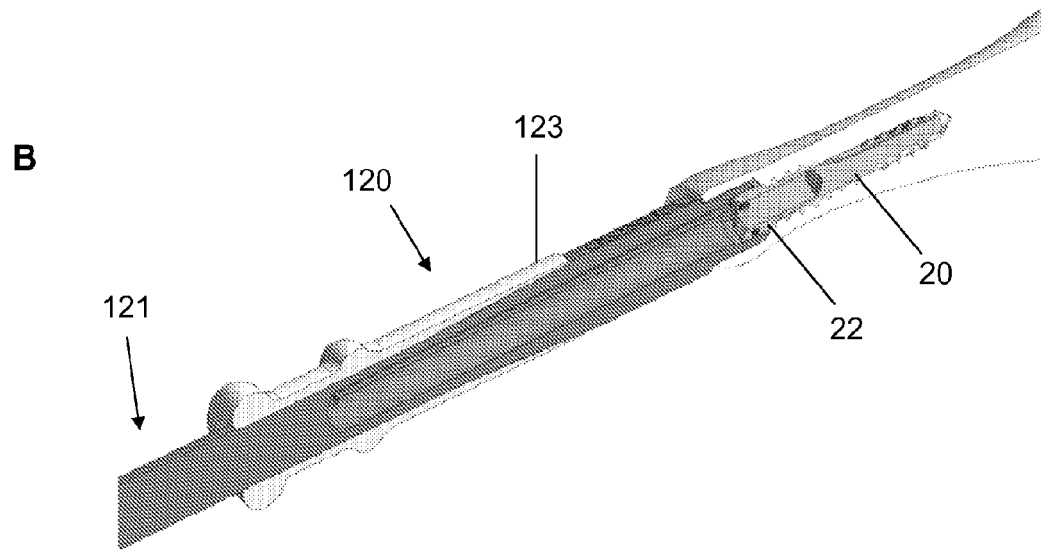
Figure 27:
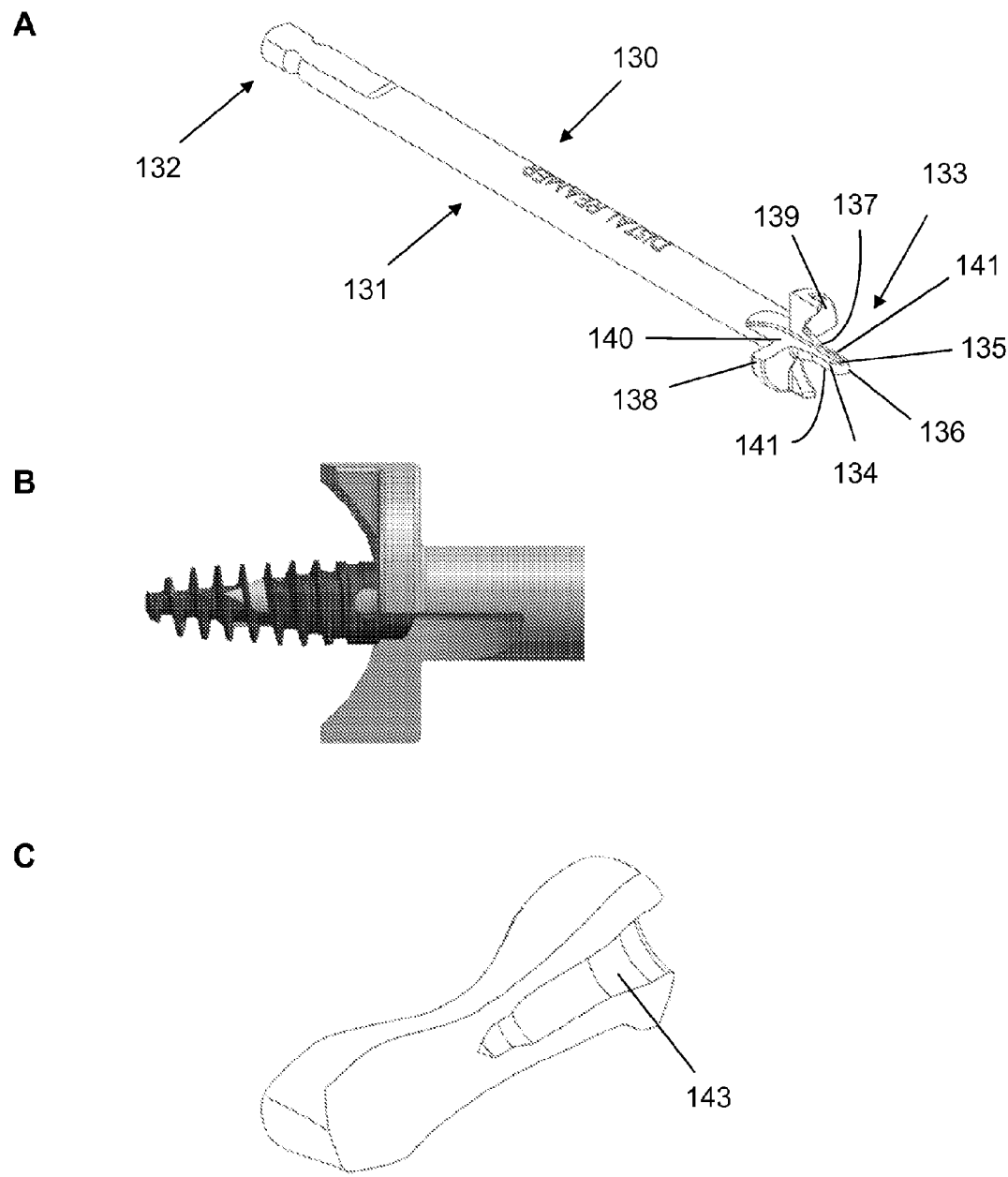
FIG. 27 is a perspective view of one embodiment of a distal reamer (Panel A), a perspective view of the distal reamer aligned with a male component (Panel B) and a perspective view of a sectioned bone showing a hole drilled by the distal reamer (Panel C).
Figure 28:
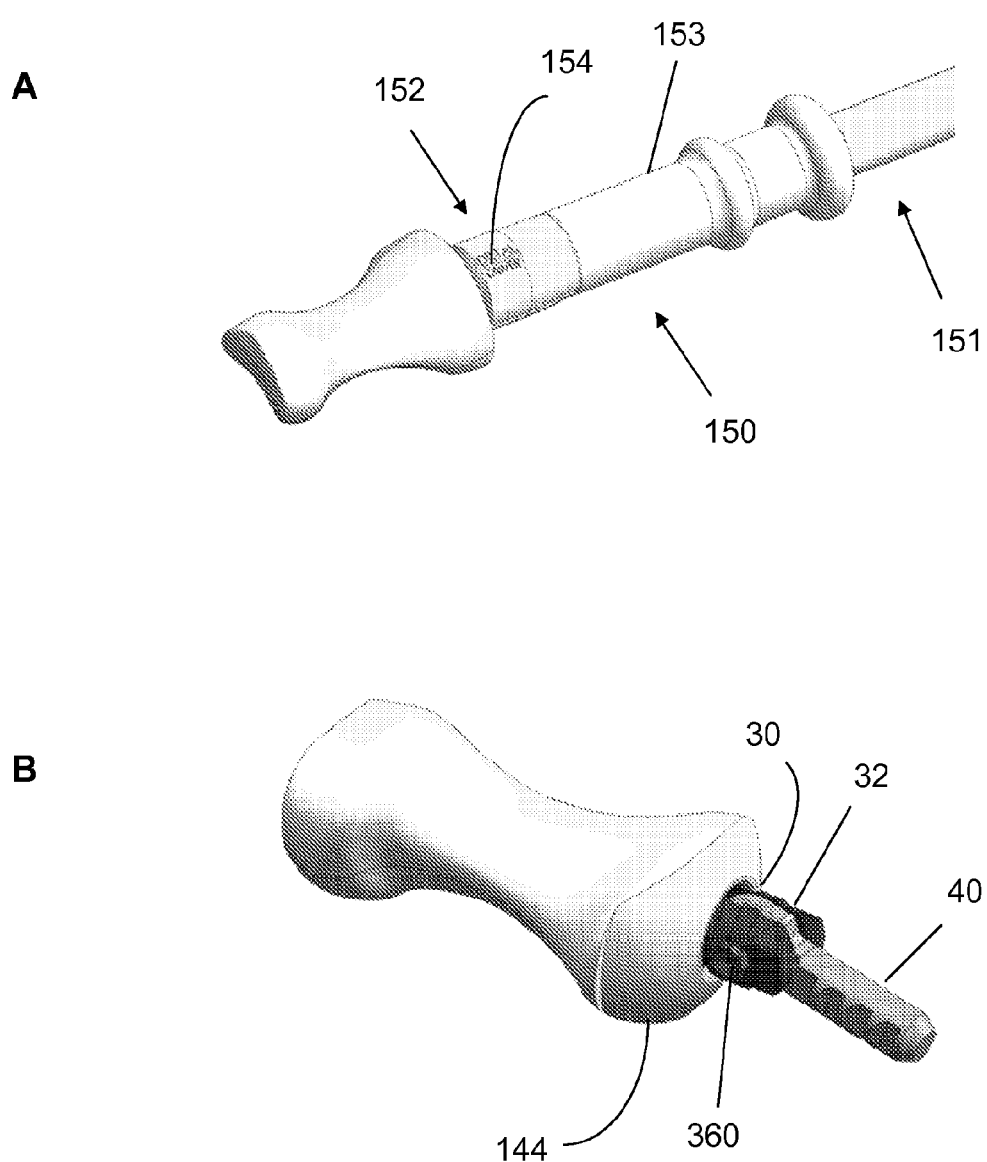
FIG. 28 is a perspective view of one embodiment of a distal driver aligned with a bone (Panel A) and a bone with a male component inserted therein.

After the proximal end of the middle phalanx is resected, a pilot hole is drilled about 9 mm deep into the intramedullary canal of the bone, using any suitable tool, for example the pilot drill 90 shown in FIG. 24. The hole for the male component 30 can then be prepared using any suitable tool, for example the distal reamer 130 illustrated in FIG. 27A. That distal reamer 130 comprises an elongate second shank 131 having a second proximal end 132 and a second distal end 133. The second proximal end can comprise a handle or can be configured to join to a separate handle, for example the quick connect handle 160 illustrated in FIG. 34. The second distal end 133 comprises a second shaping drill end 134 terminating in a second point 136. Just proximal to the second point 136 is a plurality of second ridges 135 having sharp edges designed to cut the hole illustrated in FIG. 27C. Proximal to the ridges is a second short shaft 134, and proximal to the second short shaft 134 is a second shoulder 137, wider than the second short shaft 134 but having a smaller diameter than the second shank 131. Proximal to the second shoulder 137, is a second skirt 138, wider than the second shoulder and having a concave second distal surface 139. The distal reamer 130 also comprises a second cutout 140, extending from the plurality of second ridges 135, through the second short shaft 134, the second shoulder 137, and the second skirt 138. The second cutout 140 has sharp lateral edges 141 designed to cut through the bone as the distal reamer 130 is rotated and driven therein.

In the illustrated embodiment, the second short shaft 134, the second shoulder 137, and the second skirt 138 are shorter than the counterparts on the proximal reamer 100 because the male component 30, which is driven into the hole 143 (FIG. 27) made by the distal reamer 130, is shorter than the female component 40, which is driven into the hole made by the proximal reamer 100.

The hole 143 cut by the distal reamer 130 (FIG. 27C), preferably has a diameter smaller than the diameter of the spiraling thread 34 of the male component 30, such that when the male component 30 is screwed into the hole, the spiraling thread 34 will drive through the intramedullary canal of the phalanx. FIG. 27B shows an example of the alignment of the male component 30 with a suitable distal reamer 130, where the second ridges 135 and the second short shaft 134 have a diameter of 2.0 mm, while the spiraling thread 34 of the male component 30 has a diameter of 2.2 mm. The distal reamer 130 also reams a convex surface 144 (FIG. 28) in the face of the bone. In these embodiments, the convex surface radius is 6 mm and thus significantly smaller radius than the 15 mm concave radius of the proximal bone. This allows for articulation of the toe even with a slight misalignment.

Once the hole in the proximal end of the middle phalanx is prepared, e.g., by the distal reamer 130, the male component 30 can be inserted. That insertion can be prepared using any suitable tool. A suitable tool for that purpose is the distal driver 150, partially illustrated in FIG. 28A. The proximal driver 150 comprises an elongate second shank 151 having a second proximal end (not shown) and a second distal end 152. The second proximal end can comprise a handle or can be configured to join to a separate handle, for example the quick connect handle 160 illustrated in FIG. 34. The second shank 151 comprises a second slidable bobbin 153. The second distal end 152 of the distal driver 150 comprises two second half sections (not shown) operably linked to the second bobbin 153 such that sliding the second bobbin 153 forward forces these two second half sections together to hold the second top 32 of the male component 30 securely. In some embodiments, the second distal end 152 of the distal driver 150 comprises a second marking 154 (e.g., a laser marking) that aligns with a marking on the first top 32 of the male component 30 to easily align the distal driver 120 with the male component 30.

The first top 32 of the female component 30 is placed in the distal driver 150, preferably with the connector 40 already attached, and the second bobbin 153 is slid forward to securely hold the first top 32. The first top 32 is placed in the distal driver 150 such that the second marking 154 on the distal driver 150 lines up with the marking on the first top 32. The male component 30 is then screwed into the middle phalanx until the locking pin 360 or crimping pin 33 (whichever is used) is even with the hole and the second marking is facing upwards.

The connector 40 can be adjusted to the desired angle in relation to the second top 32 at this point and the locking pin 360 or crimping pin 33 can be engaged. Alternatively, the connector 40 can be partially pushed into the female component 20 before the locking pin 360 or crimping pin 33 is engaged. If the surgeon decides not to engage the locking pin 360 or crimping pin 33, thus allowing for joint movement, the connector 40 can be fully inserted into the female component 20.

FIG. 29 shows the alignment of the two bones after insertion of the device. FIG. 30 shows the device in cross section when partially engaged; FIG. 31 shows the fully engaged device in cross section.

Figure 32:
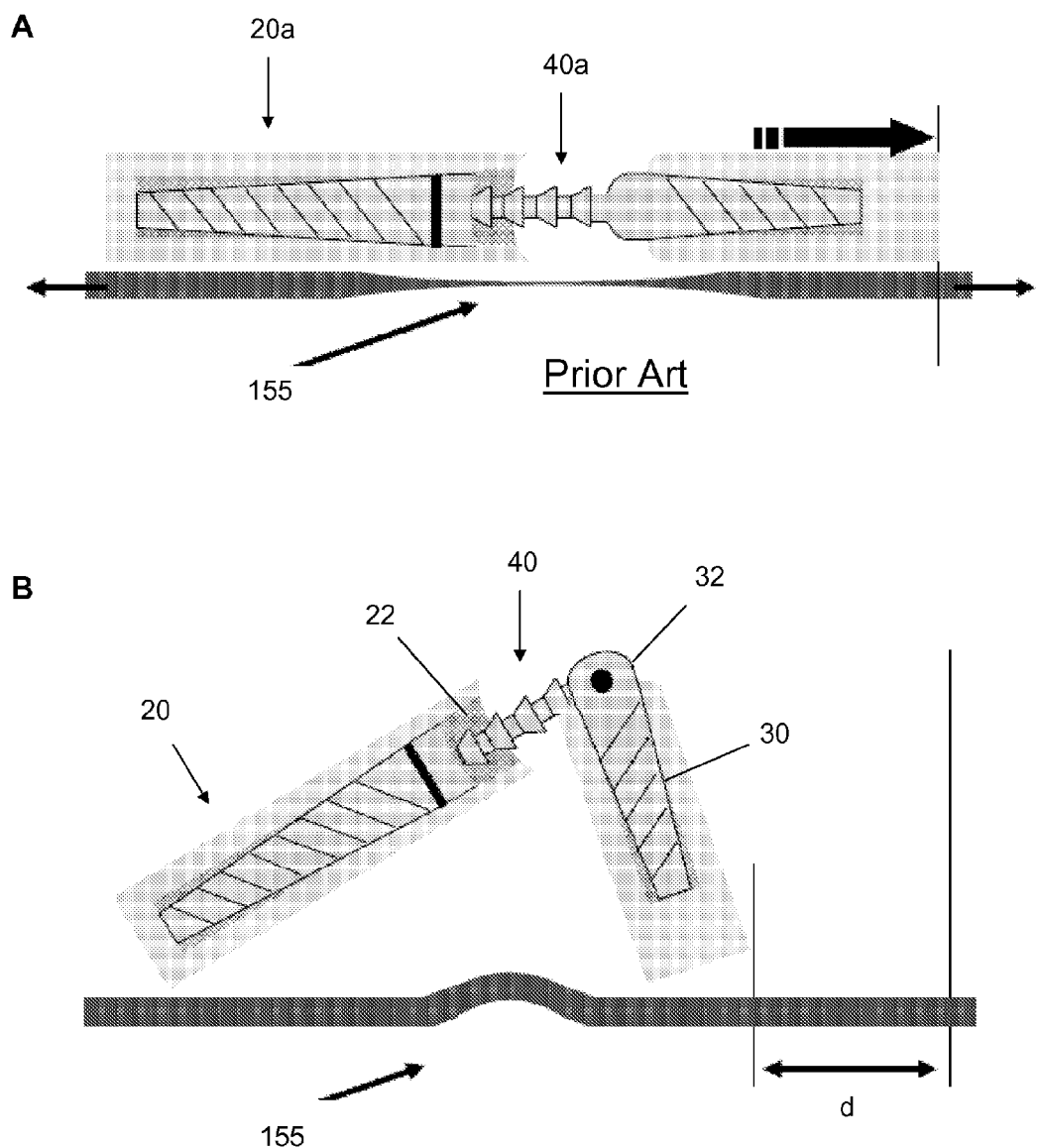
FIG. 32 is a cross section of the insertion of the two parts of a prior art device (Panel A) and the invention bone joining device (Panel B) showing the comparative stretching of surrounding tissues during the insertion of each device.

The ability of the connector 40 to rotate in relation to the second top 32 provides an advantage in inserting the devices described herein over similar prior art devices not having that ability, as shown in FIG. 32. With similar prior art devices, the two bones to be joined (e.g., the proximal and middle phalanges) must be pulled apart far enough for the central portion 42a (analogous to the connector 40 of the instant device) to be inserted into the female portion 20a (FIG. 32A). The tissue connecting the two bones, e.g., blood vessel 155, must be stretched when the bones are pulled apart, potentially causing damage to the tissues. With the devices described herein, however, before the connector 40 is inserted into the female portion 20 from the first top 22, the connector 40 can be rotated in relation to the second top 32, as shown in FIG. 32B. The two bones thus need not be pulled apart as far as with the prior art devices. Distance d in FIG. 32B shows the reduction in this potentially damaging stretching that is saved over the prior art device when the present devices are used, minimizing tissue damage and making the insertion of the connector 40 into the female component 20 easier.

Figure 33:
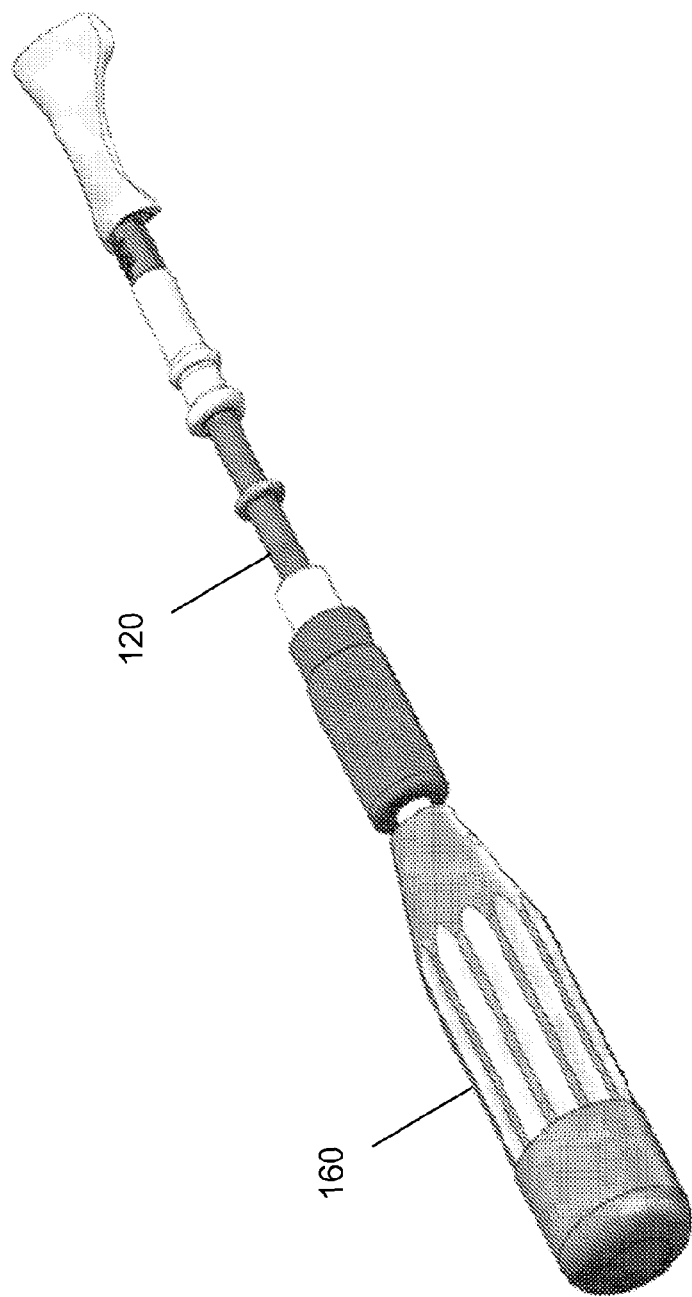
FIG. 33 is a perspective view of a proximal driver with a handle during insertion of the invention bone joining device into a proximal phalanx.
Figure 34:
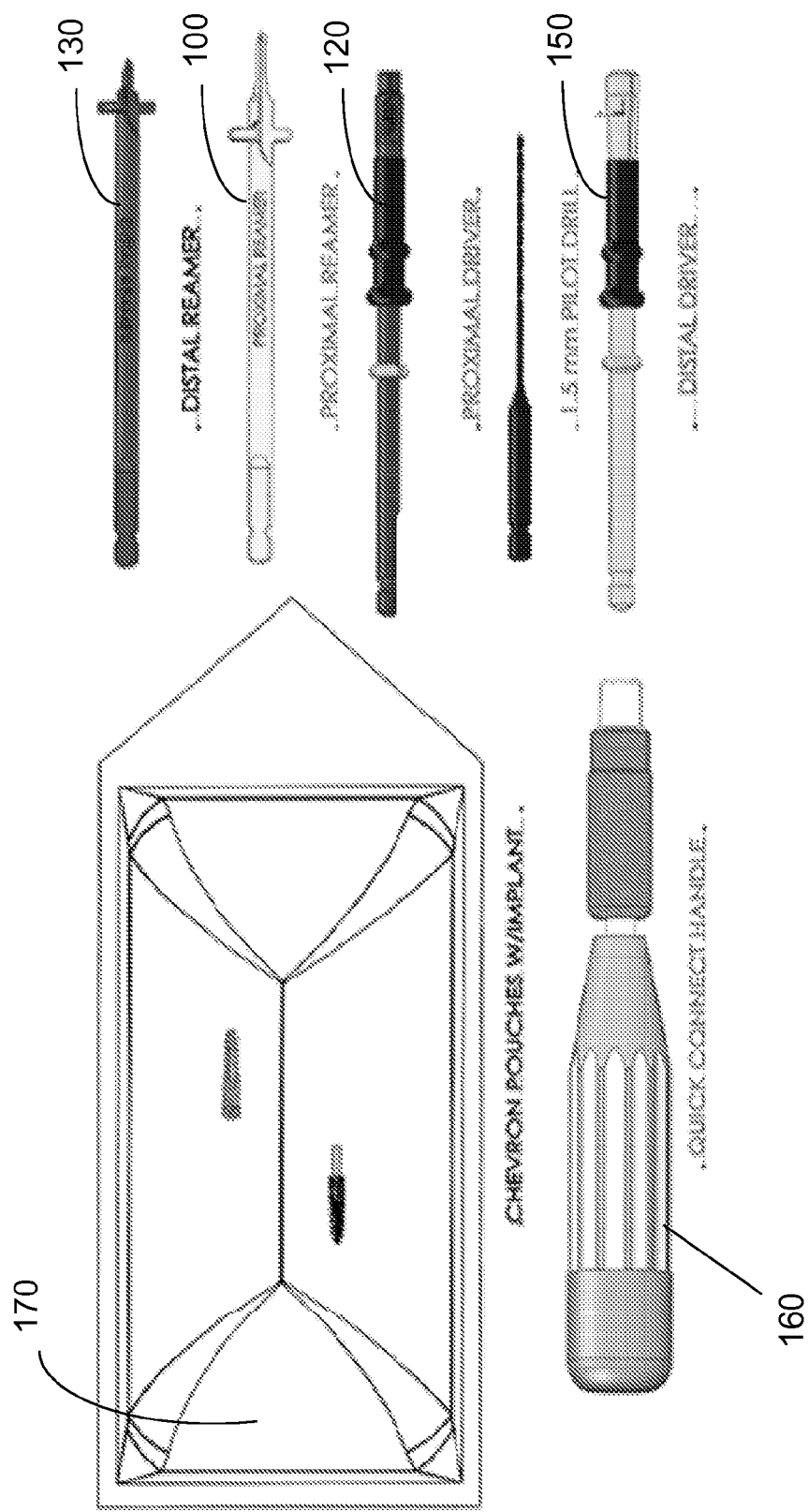
FIG. 34 is a perspective view of the invention bone joining device and tools used to install the device as prepared for packaging.

As discussed above, the proximal reamer 100, the proximal driver 120, the distal reamer 130 and the distal driver 150 can each have their own handle or can utilize a common handle, for example the quick connect handle 160 illustrated in FIG. 34. Connecting means for such handles are known in the art. FIG. 33 shows the quick connect handle in use with the proximal driver 120. In some embodiments, the elongate shank of any of these tools can comprise gripping elements, e.g., a rubber grip, to allow the surgeon to use the tool without a handle while maintaining a firm grip on the tool.

In some embodiments, any of the proximal or distal reamer or proximal or distal driver can comprise, on its proximal end the cutting portion of a proximal or distal reamer or proximal or distal driver. For example, the proximal reamer (comprising a shaping drill end with a convex first distal surface 109 at its distal end) can comprise the shaping drill end of the distal reamer (comprising a shaping drill end with a concave second distal surface 139) at is proximal end. Alternatively, the proximal reamer can comprise at its proximal end the slidable bobbin 123 and the two first half sections operably linked to the bobbin of the proximal driver. Any combination tool independently having, at its proximal and distal ends, any of the shaping drill end of the proximal or distal reamer or the bobbin and two half sections of the proximal or distal driver is envisioned herewith. Thus, multiple tools may be combined into a single tool, e.g., with one end for reaming and the other end for driving. The portion of the handle between the two tools may have grooves, cross hatching, or a gripping material to provide gripping capabilities for the person using the tools.

The each, any or all of the various tools described herein, including the pin locking tool 60, can also be provided sterilized in a package, such as a molded sterilization tray. Additionally, the bone fixation device 10, in any embodiment described above, can be packaged in a sterile package as appropriate, for example in a chevron pouch 170, as shown in FIG. 34.

Additionally, the various bone joining devices described above may include templates for use when drilling, reaming, driving, inserting the device or cutting the bones. The templates are useful to ensure that the installation of the device is accomplished with precision and accuracy. For example, a template may be used to align the proximal reamer or distal reamer to the bone, such that the hole prepared by the reamer is parallel with the long axis of the bone. Such a template could comprise a component that attaches (e.g., by screws) to the end of the bone and extends outward from the bone and provide a hole to provide a straight guide for the cutting tip of the reamer. The design and preparation of such templates are known in the art.

REFERENCES

U.S. Pat. No. 7,291,175 B1
U.S. Pat. No. 7,041,106 B1
U.S. Pat. No. 6,454,808 B1
U.S. Pat. No. 6,383,223 B1
U.S. Pat. No. 6,099,571
U.S. Pat. No. 5,919,193
U.S. Pat. No. 5,810,591
U.S. Pat. No. 5,443,467
U.S. Pat. No. 5,290,314
U.S. Pat. No. 5,207,712
U.S. Pat. No. 5,062,851
U.S. Pat. No. 5,037,440
U.S. Pat. No. 4,908,031
U.S. Pat. No. 4,304,011
U.S. Pat. No. 4,246,662

U.S. Pat. No. 3,991,425
U.S. Des. 277,784
US 2006/0074492 A1
US 2006/0052878 A1
US 2004/0220678 A1
EP 831757 B1
WO 1997/016137 A1
WO 1996/005784 A1
WO 1993/009728
JP 2005-073740 A
DE 19949890 A1
GB 2126097 A
GB 1582974 A
Hetherington V J 2000, Metararsalgia and lesser metatarsal surgery, pp. 429-451 in Textbook of Hallux Valgus and Forefront Surgery, Vincent J. Hetherington, Ed.
Murray P M, 2007, Surface Replacement Arthroplasty of the Proximal Interphalangeal Joint, The Journal of Hand Surgery 32:899-904.
Sokolow C, 2006, Une prothèse de l'articulation interphalangienne proximale ostéo-intégrée: IPP 2. Premiers resultants—Short term results of the IPP 2 proximal interphalangeal joint prosthesis, Chirurgie de la Main 25: 280-285.
Iselin F, Pradet G, Gouet O 1988, Désarthrodèses-arthroplasties interphalangiennes proximales—Conversion to Arthroplasty from Proximal Interphalangeal Joint Arthrodesis, Annales de Chirurgie de la Main 7: 115-119.
Konkel K F, Menger A G, Retzlaff S A 2007, Hammer toe correction using an absorbable intramedullary pin, Foot & Ankle International 28:916-920.
Caterini R, Farsetti P, Tarantino U, Potenza V, Ippolito E 2005, Arthrodesis of the toe joints with an intramedullary cannulated screw for correction of hammertoe deformity, Foot & Ankle International 25:256-261.
Edwards W H, Beischer A D 2002, Interphalangeal joint arthrodesis of the lesser toes, Foot & Anlle Clinics North America 7:43-48.
www.sgarlatolabs.com/products_ship_implant.shtml
www.bioproimplants.com/extremities_lower.asp
www.medcompare.com/details/32380/Flexible-Dig In view of the above, it will be seen that the several advantages of the application are achieved and other advantages attained.

As various changes could be made in the above methods and compositions without departing from the scope of the application, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A bone coupling device for coupling a first bone piece to a second bone piece, the device comprising:
a first component comprising a wall portion, a first cavity defined by an interior surface of the wall portion, a first indentation extending into an exterior surface of the wall portion, at least one aperture extending through the wall portion from within the first indentation and to the first cavity, and a first stem portion for coupling with the first bone piece;
a second component comprising a second stem portion for coupling with the second bone piece and an axially extending connector portion angularly offset from the second stem portion and configured to be positioned within the first cavity, the connector portion including a plurality of second indentations that are arranged along an axis of the connector portion; and
a coupling member including at least one knob, the coupling member being positioned within the first indentation of the first component and extending through the at least one aperture such that the at least one knob is at least partially positioned within the first cavity,
wherein in a first orientation of the first and second components with the connector portion of the second component positioned within the first cavity of the first component, the at least one knob is at least partially retracted from the first cavity and abuts an outer surface of the connector portion adjacent to a second indentation, and
wherein in a second orientation of the first and second components with the connector portion of the first component positioned within the first cavity of the first component, the coupling member portion is in a contracted state as compared to the first orientation such that the least one knob is positioned within at least one of the second indentations and thereby coupling the first and second components.

2. The device of claim 1, wherein the connector portion of the second component includes two sets of a plurality of axially disposed second indentations along differing sides of the connector portion, wherein the coupling member includes two knobs, and wherein the first indentation of the first component includes two apertures extending to the first cavity configured to accept the two knobs therein.

3. The device of claim 1, wherein the first and second orientations of the first and second components are differing axial and/or rotational orientations of the first and second components with respect to each other.

4. The device of claim 1, wherein the connector portion of the second component extends from a first end of the second component in a first axial direction, and wherein the second indentations are spaced along the first axial direction from each other.

5. The device of claim 4, wherein the second indentations include a distal edge proximate the first end of the second component, and wherein the distal edge of the second indentations extends substantially perpendicular from the outer surface of the second component or is sloped at an acute angle from the outer surface of the second component toward the first end to substantially prevent the connector portion of the second component from translating in a second axial direction that substantially opposes the first axial direction.

6. The device of claim 4, wherein the second indentations include a proximal edge that is distal the first end of the second component and substantially opposes the distal edge thereof, and wherein the proximal edge of the second indentations is sloped at an acute angle from the outer surface of the second component toward the first end to guide the at the least one knob positioned within a second indentation out of the second indentation in the first axial direction.

7. The device of claim 4, wherein, in the second orientation, the least one knob being positioned within at least one of the second indentations limits the relative rotation of the first and second components with respect to each other, and substantially prevents the connector portion of the first component from translating out from the first cavity of the first component in a second axial direction substantially opposing the first axial direction.

8. The device of claim 7, wherein, in the first and second orientations, the connector portion of the first component is translatable in the first axial direction to insert the connector portion further into the cavity of the first component.

9. The device of claim 1, wherein the cavity of the first component and outer surface of the connector portion of the second component are substantially cylindrical, and wherein the outer surface of the connector portion extends substantially about the plurality of axially disposed second indentations.

10. The device of claim 9, wherein coupling member is a spring clip that extends about the outer surface of the connector portion of the second component, and wherein the spring clip is oriented substantially perpendicular to the axis of the axially extending connector portion.

11. The device of claim 1, wherein the entirety of the coupling member is positioned below or even with an exterior surface of the first component that extends about the first indentation thereof.

12. A method of coupling a first bone piece to a second bone piece, the method comprising:
    coupling a first stem portion of a first component with the first bone piece, the first component including
    a wall portion, a first cavity defined by an interior surface of the wall portion, and a first indentation extending into an exterior surface of the wall portion, and at least one aperture extending through the wall portion from within the first indentation and to the first cavity;
    coupling a second stem portion of a second component with the second bone piece, the second component including an axially extending connector portion angularly offset from the second stem portion and configured to be positioned within the first cavity of the first component, the connector portion including a plurality of second indentations that are arranged along an axis of the connector portion;
    positioning the connector portion of the second component within the first cavity of the first component such that the at least one aperture of the first component is substantially aligned with a first portion of the outer surface of the connector portion; and
    substantially aligning the at least one aperture of the first component with at least one of the second indentations of the connector portion.

13. The method of claim 12, wherein substantially aligning the at least one aperture of the first component with at least one of the second indentations contracts a coupling member that is positioned within the first indentation of the first member such that the coupling member extends through the least one aperture and into the first cavity.

14. The method of claim 13, wherein contracting the coupling member positions at least one knob of the coupling member into at least one of the second indentations to couple the first and second components.

15. The method of claim 12, wherein positioning the connector portion of the second component within the first cavity of the first component such that the at least one aperture of the first component is substantially aligned with a first portion of the outer surface of the connector portion expands a coupling member that is positioned within at least one of the second indentations.

16. The method of claim 15, wherein expanding a coupling member includes positioning at least one knob of the coupling member into abutment with an outer surface of the connector portion that is adjacent to at least one of the second indentations.

17. The method of claim 12, further including adjusting the relative orientation of the first and second components by rotating and/or axially translating the first and second components with respect to each other from a first orientation, wherein the at least one aperture is substantially aligned with at least one of the second indentations to a second orientation, wherein the at least one aperture is substantially aligned with a second portion of the outer surface of the connector portion that is adjacent to at least one of the second indentations.

18. The method of claim 17, further including adjusting the relative orientation of the first and second components by rotating and/or axially translating the first and second components with respect to each other from the second orientation to a third orientation, wherein the at least one aperture is substantially aligned with at least one of the second indentations.

19. The method of claim 12, wherein positioning the connector portion of the second component within the first cavity of the first component such that the at least one aperture of the first component is substantially aligned with a first portion of the outer surface of the connector portion, and substantially aligning the at least one aperture of the first component with at least one of the second indentations to couple the first and second components includes axially translating the connector portion of the second within the first cavity of the first component.

20. The method of claim 12, wherein the first stem portion and second stem portion include external threads, wherein coupling a first stem portion of a first component with the first bone piece includes threadably coupling the first stem portion to the first bone piece via the external threads of the first stem portion, and wherein coupling a second stem portion of a second component with the second bone piece includes threadably coupling the second stem portion to the second bone piece via the external threads of the second stem portion.

* * * * *